US009605941B2

(12) United States Patent
Ozcan et al.

(10) Patent No.: US 9,605,941 B2
(45) Date of Patent: *Mar. 28, 2017

(54) LENS-FREE TOMOGRAPHIC IMAGING DEVICES AND METHODS

(75) Inventors: Aydogan Ozcan, Los Angeles, CA (US); Serhan O. Isikman, Los Angeles, CA (US); Waheb Bishara, Menlo Park, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 336 days.

This patent is subject to a terminal disclaimer.

(21) Appl. No.: 13/976,197

(22) PCT Filed: Jan. 5, 2012

(86) PCT No.: PCT/US2012/020366
§ 371 (c)(1),
(2), (4) Date: Jun. 26, 2013

(87) PCT Pub. No.: WO2012/094523
PCT Pub. Date: Jul. 12, 2012

(65) Prior Publication Data
US 2013/0280752 A1 Oct. 24, 2013

Related U.S. Application Data

(60) Provisional application No. 61/430,465, filed on Jan. 6, 2011, provisional application No. 61/486,685, filed on May 16, 2011.

(51) Int. Cl.
*G01B 9/02* (2006.01)
*G01N 21/47* (2006.01)
(Continued)

(52) U.S. Cl.
CPC ..... *G01B 9/02041* (2013.01); *G01N 21/4795* (2013.01); *G03H 1/0443* (2013.01);
(Continued)

(58) Field of Classification Search
CPC . G01N 2223/419; G01N 23/046; A61B 6/032
(Continued)

(56) References Cited

U.S. PATENT DOCUMENTS

| 4,349,740 A | 9/1982 | Grassmann et al. |
| 6,236,708 B1 | 5/2001 | Lin et al. |

(Continued)

FOREIGN PATENT DOCUMENTS

| JP | 07-134135 | 5/1995 |
| JP | 2004-532405 A | 10/2004 |

(Continued)

OTHER PUBLICATIONS

Ting-Wei Su, Serhan O. Isikman, Waheb Bishara, Derek Tseng, Anthony Erlinger, and Aydogan Ozcan, "Multi-angle lensless digital holography for depth resolved Imaging on a chip", Opt Express, vol. 18, No. 9, pp. 9690-9711, 2010.*

(Continued)

*Primary Examiner* — Gims Philippe
*Assistant Examiner* — Ayman Abaza
(74) *Attorney, Agent, or Firm* — Vista IP Law Group LLP

(57) ABSTRACT

A lens-free system for the three-dimensional imaging of objects contained within a sample places a sample holder between an image sensor and an illumination source, with the sample-sensor distance being much smaller than the sample-illumination source distance. Holographic images are taken at different angles as well as different lateral jogs within a single angle and are reconstructed into a three (Continued)

dimensional image of objects within the sample. The system may be a hand held, portable unit.

7 Claims, 19 Drawing Sheets

(51) Int. Cl.
G03H 1/04 (2006.01)
G03H 1/08 (2006.01)
G03H 1/26 (2006.01)
G03H 1/02 (2006.01)
G03H 1/00 (2006.01)

(52) U.S. Cl.
CPC .......... *G03H 1/0866* (2013.01); *G03H 1/265* (2013.01); *G03H 2001/005* (2013.01); *G03H 2001/0212* (2013.01); *G03H 2001/046* (2013.01); *G03H 2001/0447* (2013.01); *G03H 2210/30* (2013.01); *G03H 2210/62* (2013.01); *G03H 2222/24* (2013.01); *G03H 2222/34* (2013.01); *G03H 2223/16* (2013.01); *G03H 2227/02* (2013.01); *G03H 2227/03* (2013.01); *G03H 2240/56* (2013.01)

(58) Field of Classification Search
USPC .......................................................... 348/79
See application file for complete search history.

(56) References Cited

U.S. PATENT DOCUMENTS

| | | | |
|---|---|---|---|
| 7,466,790 B2* | 12/2008 | Suryanarayanan et al. | 378/4 |
| 7,817,773 B2* | 10/2010 | Stanton | A61B 6/466 378/15 |
| 8,866,063 B2* | 10/2014 | Ozcan | G02B 21/00 250/216 |
| 2004/0264637 A1* | 12/2004 | Wang | G21K 7/00 378/43 |
| 2007/0183559 A1 | 8/2007 | Hempel | |
| 2008/0005844 A1* | 1/2008 | Tybinkowski et al. | 5/661 |
| 2008/0095312 A1* | 4/2008 | Rodenburg | G01T 1/2914 378/87 |
| 2008/0101537 A1 | 5/2008 | Sendai | |
| 2008/0259345 A1* | 10/2008 | Fukutake | 356/450 |

FOREIGN PATENT DOCUMENTS

| | | |
|---|---|---|
| JP | 2007-536552 A | 12/2007 |
| WO | 02/080090 A1 | 10/2002 |
| WO | 2005/108917 A2 | 11/2005 |

OTHER PUBLICATIONS

Yuli Wang, Mark Bachman, Guann-Pyng Li, Shuguang Guo, Brian J. F. Wong, and Zhongping Chen, "Low-voltage polymer-based scanning cantilever for in vivo optical coherence tomography", Optics Letters, vol. 30, No. 1, 2005.*
J. Garcia-Sucerquia, W. Xu, S. K. Jericho, P. Klages, M. H. Jerichoand H.J. Kreuzer, "Digital in-line holographic microscopy", Appl. Opt., 2006, 45, 836-850.*
Sungkyu Seo, Ting-Wei Su, Derek K. Tseng, Anthony Erlingera and Aydogan Ozcan, "Lensfree holographic imaging for on-chip cytometry and diagnostics", Lab Chip, 2009, vol. 9, No. 6, pp. 777-787.*
Aydogan Ozcan, Sungkyu Seo, Ting-wei Su, Anthony Erlinger, Derek Tsenga, "Lens-Free On-chip Cytometry for Wireless Health Diagnosis", IEEE Leos Newsletter, Oct. 2008.*
Yule Wang, Mark Bachman, Guann-Pyng Li, Shuguang Guo, Brian J. F. Wong, and Zhongping Chen, "Low-voltage polymer-based scanning cantilever for in vivo optical coherence tomography", Optics Letters, vol. 30, No. 1, 2005.*
Hardie et al., Joint MAP Registration and High-Resolution Image Estimation Using a Sequence of Undersampled Images, IEEE, vol. 6 No. 12, Dec. 1997.
Ozcan et al., Ultra wide-filed lens-free monitoring of cells on-chip, Lab on Chip 8, 89-106, Nov. 1, 2007.
Ozcan et al., Lens-free On-Chip Cytometry for wireless Health Diagnosis, IEEE LEOS Newsletter, Oct. 2008.
Seo et al., Lensfree On-chip Cytometry Using Tunable Monochromatic Illumination and Digital Noise Reduction, Multi-color Lucas, Sep. 2008.
Seo et al., Lensfree holographic imaging for on-chip cytometry and diagnostics, Lab on a Chip, 9, 777-787, Dec. 5, 2008.
Su et al., Towards Wireless Health: Lensless On-Chip Cytometry, Biophotonics, Dec. 2008.
Su et al., High-Throughput Lensfree Imaging and Characterization of Heterogeneous Cell Solution on a Chip, Biotechnology and Bioengineering, Sep. 8, 2008.
Isikman et al., Lensfree Cell Holography On a Chip: From Holographic Cell Signatures to Microscopic Reconstruction, LEOS Annual Meeting Conf. Proceedings, Oct. 2009.
Mudanyali et al., Lensless On-chip Imaging of Cells Provides a New Tool for High-throughput Cell-Biology and Medical Diagostics, Journal of Visualized Experiments, Dec. 14, 2009.
Bishara et al., Lensfree on-chip microscopy over a wide field-of-view using pixel super-resolution, Optics Express, vol. 18 No. 11, May 24, 2010.
Coskun et al., Wide field-of-view lens-free fluorescent imaging on a chip, Lab Chip, 10(7), 824-827, Apr. 7, 2010.
Coskun et al., Lensless wide-field fluorescent imaging on a chip using compressive decoding of sparse objects, Optics Express, vol. 18 No. 10, May 5, 2010.
Khademhosseinieh et al., Lensfree color imaging on a nanostructured chip using compressive decoding, Applied Physics Letters, 97, 211112-1, Nov. 24, 2010.
Khademhosseinieh et al., Lensfree on-chip imaging using nanostructured surfaces, Applied Physics Letters, 96, 171106, Apr. 30, 2010.
Mudanyali et al., Compact, light-weight and cost-effective microscope based on lensless incoherent holography for telemedicine applications, Lab Chip, 10, 1417-1428, Apr. 19, 2010.
Ozcan, Smart technology for global access to healthcare, SPIE, Mar. 16, 2010.
Ozcan et al., Lensfree on-chip holography facilitates novel microscopy applications, SPIE, May 19, 2010.
Mastronarde, David N., Dual-Axis Tomography: An Approach with Alignment Methods That Preserve Resolution, Journal of Structural Biology 120:343-352 (1997).
Mudanyali, Onur et al., Detection of waterborne parasites using field-portable and cost-effective lensfree microscopy, Lab Chip, 2010, 10, 2419-2423.
Mudanyali, Onur et al., Compact, Light-weight and Cost-effective Microscope based on Lensless Incoherent Holography for Telemedicine Applications, Lab Chip 10:1417-1428 (2010).
Radermacher, Michael, Weighted back-projection methods, Electron Tomography: Methods for three dimensional visualization of structures in the cell, (Springer, New York, 2nd ed.) pp. 245-273(2006).
Su, Ting-Wei et al., Multi-angle lensless digital holography for depth resolved imaging on a chip, Apr. 26, 2010, vol. 18, No. 9, Optics Express, 9690-97.
PCT International Search Report for PCT/US2012/020366, Applicant: The Regents of the University of California, Form PCT/ISA/210 and 220, dated Aug. 24, 2012 (5pages).
PCT Written Opinion of the International Search Authority for PCT/US2012/020366, Applicant: The Regents of the University of California, Form PCT/ISA/237, dated Aug. 24, 2012 (5pages).
Extended European Search report dated Jun. 25, 2014 in European Patent Application No. 12731935.8-1904, Applicant: The Regents of the University of California (8pages).

(56) References Cited

OTHER PUBLICATIONS

Bishara, Waheb et al., Lensfree on-chip microscopy over a wide field-of-view using pixel super-resolution, Optics Express, vol. 18, No. 11, pp. 11181-11191, May 24, 2010.
Su, Ting-Wei et al., Multi-angle lensless digital holography for depth resolved imaging on a chip, Optics Express, vol. 18, No. 9, pp. 9690-9711.
Notice of Rejection dated Oct. 30, 2015 in Japanese Patent Application No. 2013-548551 including English Translations prepared by Kita-Aoyama International Patent Bureau (10pages).

* cited by examiner

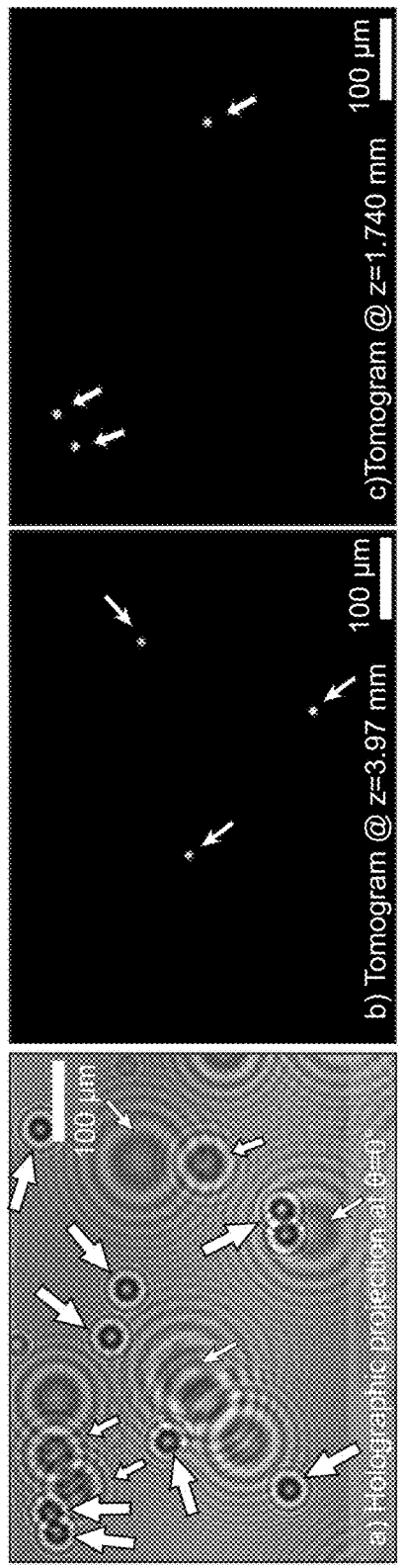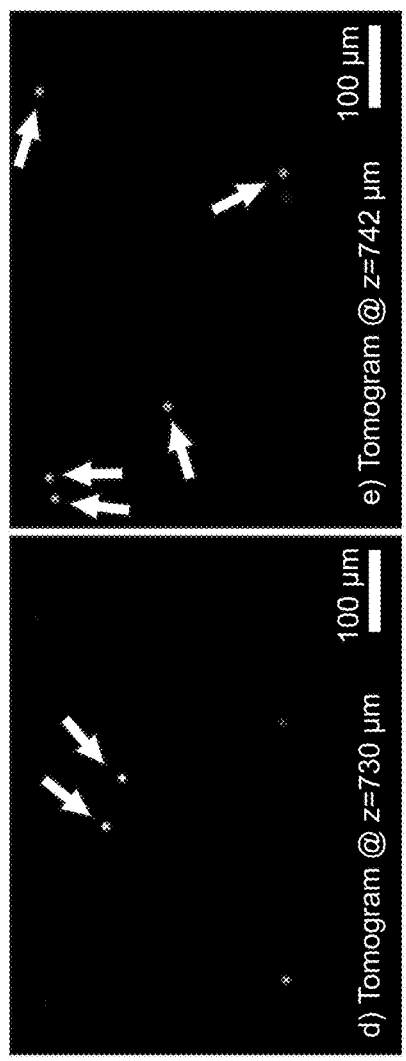

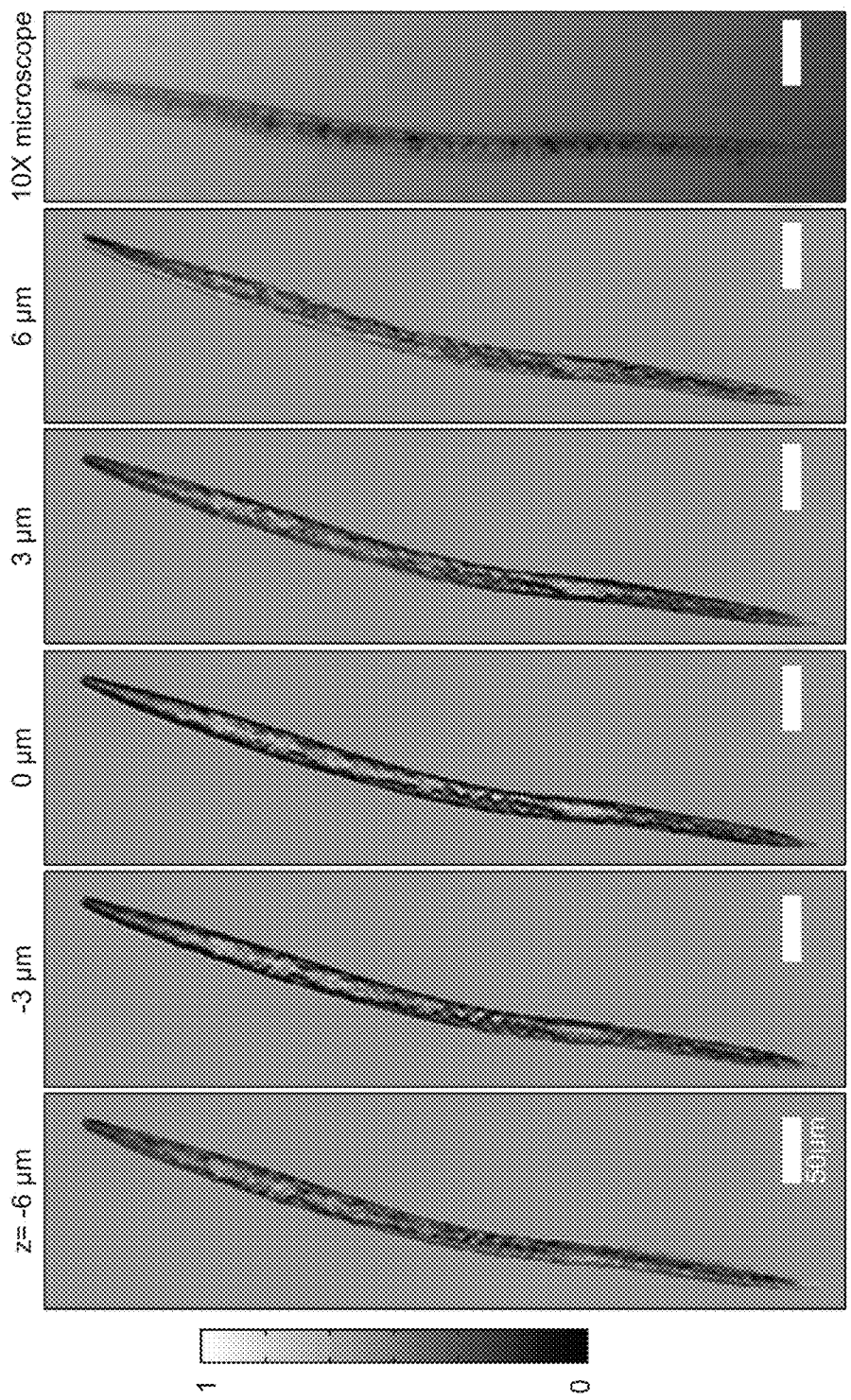

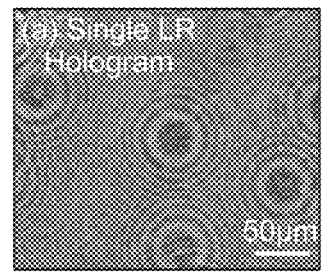 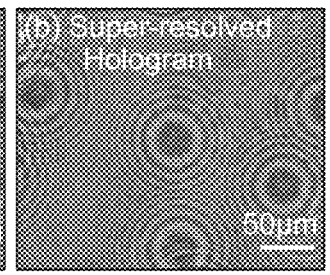
FIG. 15A  FIG. 15B
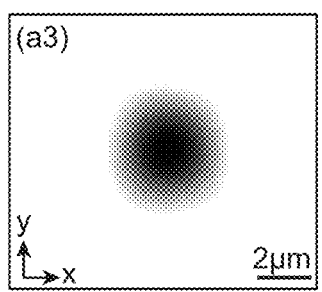 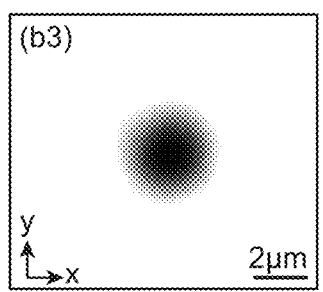
FIG. 15C  FIG. 15D
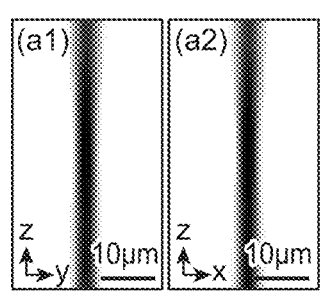 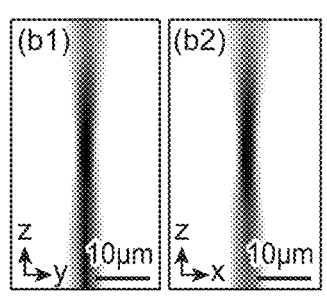
FIG. 15E  FIG. 15F
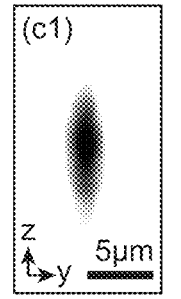 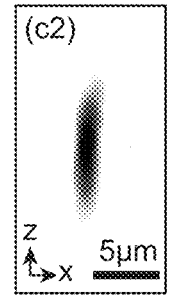 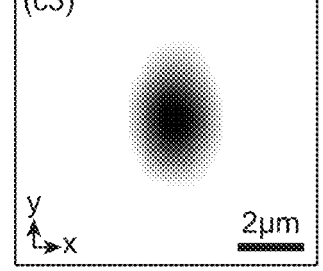
FIG. 16A  FIG. 16B  FIG. 16C

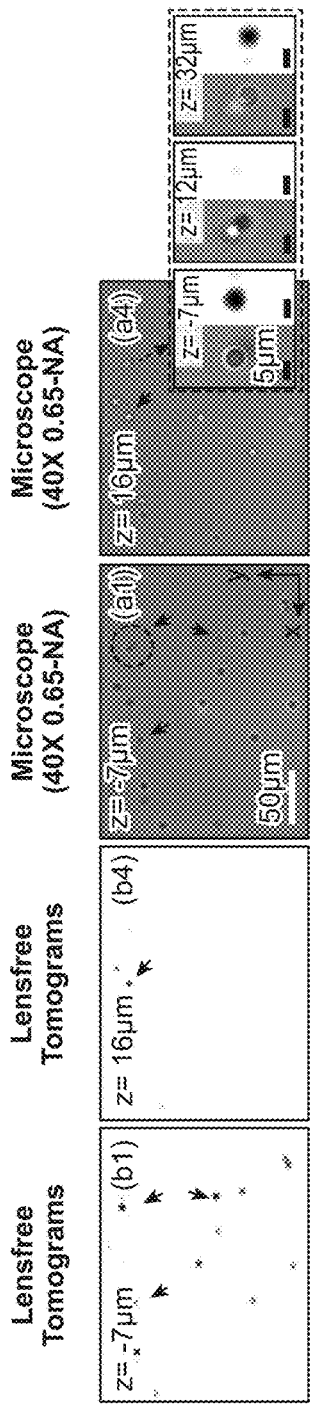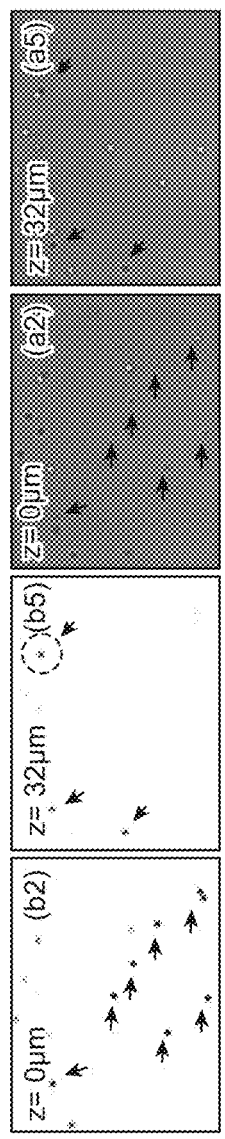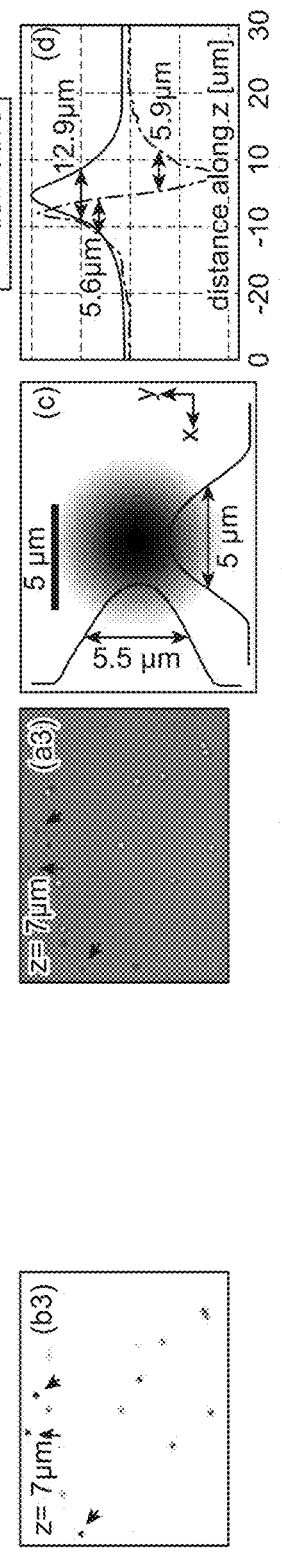
FIG. 17A FIG. 17B FIG. 17C FIG. 17D FIG. 17E FIG. 17F FIG. 17G FIG. 17H FIG. 17I FIG. 17J
FIG. 18A FIG. 18B

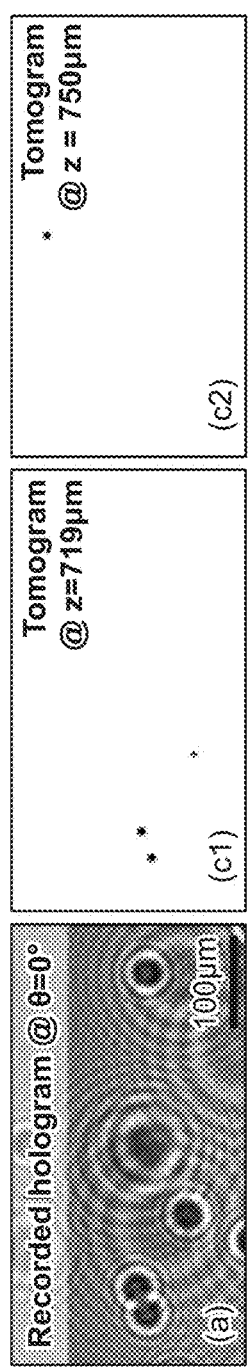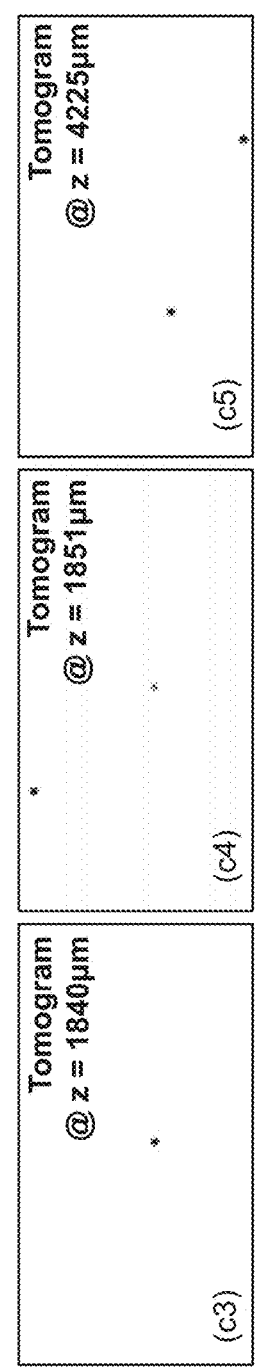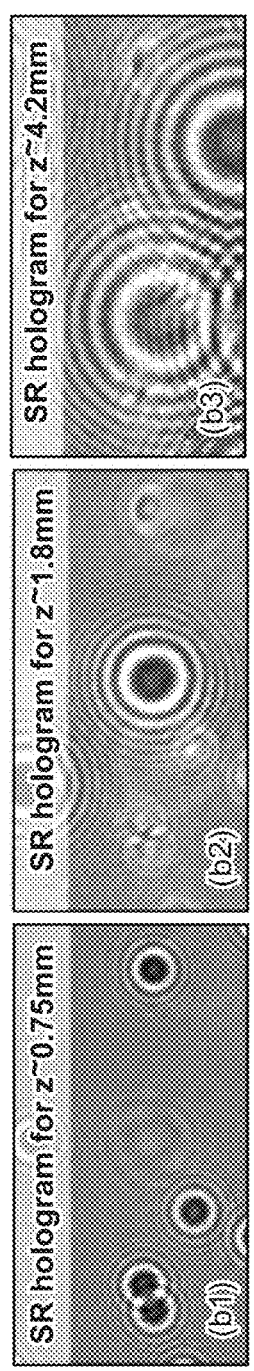
FIG. 19A — FIG. 19I

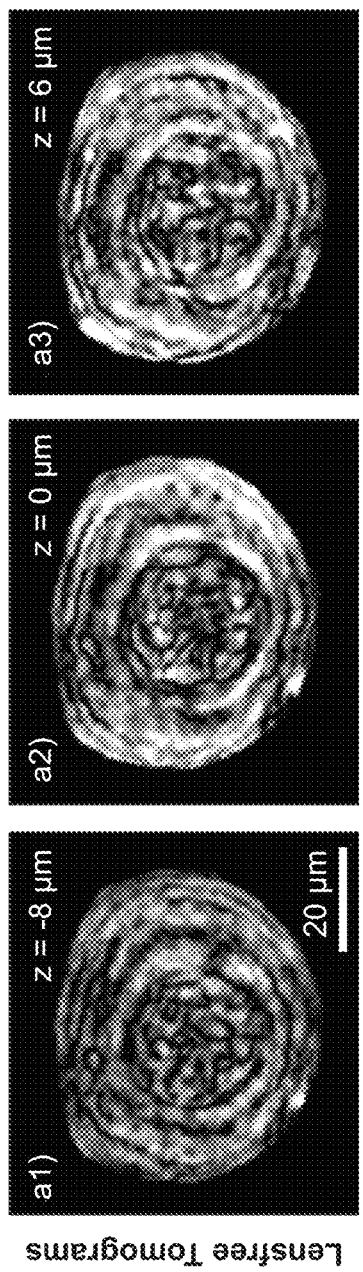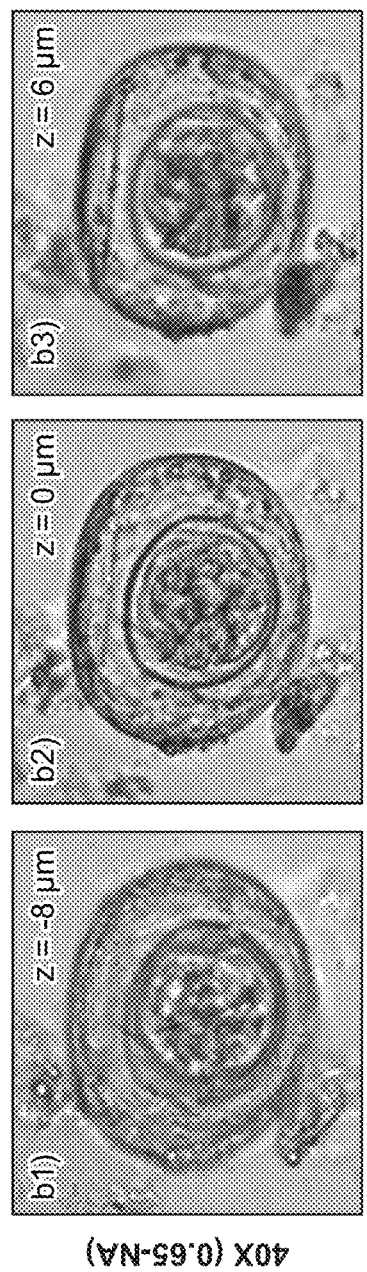
FIG. 20A
FIG. 20B

LENS-FREE TOMOGRAPHIC IMAGING DEVICES AND METHODS

RELATED APPLICATIONS

This Application is a U.S. National Stage filing under 35 U.S.C. §371 of International Application No. PCT/US2012/020366, filed Jan. 5, 2012, which claims priority to U.S. Provisional Patent Application No. 61/430,465 filed on Jan. 6, 2011 and U.S. Provisional Patent Application No. 61/486,685 filed on May 16, 2011. The contents of the aforementioned applications are hereby incorporated herein by reference in their entirely. Priority to the aforementioned applications are hereby expressly claimed in accordance with 35 U.S.C. §§119, 120, 365 and 371 and any other applicable statutes.

FIELD OF THE INVENTION

The field of the invention generally relates to methods and devices for imaging of microscopic structures such as cells. More particularly, the field of the invention pertains to systems and methods for the tomographic imaging of small particles such as cells, organelles, cellular particles and the like in a static sample or flowing within a microfluidic environment.

BACKGROUND

Light microscopy has been an irreplaceable tool in life sciences for several centuries. Nevertheless, its design has not fundamentally changed since its inception, i.e., the image of the specimen is magnified through a system of lenses and other optical components before being detected by the eye or a digital sensor array for visualization. The quest to resolve smaller features with better resolution and contrast has improved the capabilities of light microscopy at the cost of increasing its size and complexity. On the other hand, emerging technologies have flourished such as microfluidic and lab-on-a-chip systems which offer fast and efficient handling and processing of biological samples within highly miniaturized architectures. However, optical inspection of specimens is still being performed by conventional light microscopes, which has in general several orders of magnitude size mismatch compared to the scale of the microfluidic systems. As a result, there is a clear need for alternative compact microscopy modalities that are capable of integrating with miniaturized lab-on-a-chip platforms.

The urge for new optical microscopy modalities is not solely driven by the need for miniaturization and microfluidic integration. The fact that high resolution is achieved at the cost of significant field-of-view (FOV) reduction is another fundamental limitation of lens-based imaging. The relatively small FOV of conventional light microscopy brings additional challenges for its application to several important problems such as rare cell imaging or optical phenotyping of model organisms, where high throughput microscopy is highly desired.

In order to provide a complementary solution to these aforementioned needs, alternative, lens-free microscopy platforms have been developed which combines high resolution and large FOV in a compact, on-chip imaging architecture. In this modality, digital in-line holograms of microobjects are recorded on a sensor array using partially coherent illumination with unit fringe magnification such that the entire active area of the sensor serves as the imaging FOV. To overcome the resolution limitation imposed by the pixel size at the sensor, multiple sub-pixel shifted holograms of the sample are acquired, and pixel super-resolution techniques are then applied to achieve sub-micron lateral resolution without compromising the large FOV. As a result, a lateral imaging performance comparable to a microscope objective with a numerical aperture (NA) of ~0.5 has been achieved over an FOV of 24 mm$^2$, which is more than two orders-of-magnitude larger than that of an objective lens with similar resolution. See e.g., Bishara W. et al., Lensfree on-chip microscopy over a wide field-of-view using pixel super-resolution. *Optics Express* 18:11181-11191 (2010).

While pixel super-resolution techniques in partially coherent lens-free in-line holography enable imaging with sub-micron lateral resolution over a large FOV, the axial resolution is unfortunately significantly lower (e.g., >40-50 µm) due to the inherently long depth-of-focus of digital in-line holography. Accordingly, despite the fact that holographic reconstruction can be numerically focused at different depths, sectioning of planes closer than ~50 µm has not been feasible with lens-free wide-field holographic microscopes regardless of their detection numerical apertures. This fundamental limitation needs to be addressed.

Along the same lines, in recent years, there has been an increased interest in optical microscopy modalities that enable sectional imaging. As an example, Optical Projection Tomography (OPT) has been proposed, where an optically cleared specimen immersed in index-matching gel is rotated with respect to the fixed optical path of a conventional lens-based microscope, offers an isotropic resolution of ~10 µm in all three dimensions within an imaging volume of up to ~1 cm$^3$. See Sharpe J et al., Optical Projection Tomography as a Tool for 3D Microscopy and Gene Expression Studies, *Science* 296:541-545 (2002).

A modified version of OPT by using high NA objective lenses has also been implemented recently to achieve sub-micron resolution cell imaging over a significantly reduced volume of e.g., <0.0005 mm$^3$ See Fauver M et al., Three-dimensional imaging of single isolated cell nuclei using optical projection tomography, *Optics Express* 13:4210-4223 (2005).

Optical Diffraction Tomography (ODT) is another powerful technique where digital holography is utilized to reconstruct the 3D refractive index distribution of the specimen by changing the illumination direction, rotating the object, or by capturing multiple images at different wavelengths. These tomographic systems can routinely image cells potentially achieving sub-micron resolution in all three dimensions. However the trade-off between resolution and imaging volume also applies to these systems just like conventional microscopy, and high resolution is achieved at the cost of a significantly reduced imaging FOV of e.g., less than 0.04-0.2 mm$^2$ and a depth-of-field (DOF) of less than 10-20 µm depending on the objective lens that is used.

For the same purpose, another imaging modality, namely, Selective Plane Illumination Microscopy (SPIM) has also been introduced, which utilizes a light sheet generated by a cylindrical lens to successively illuminate selective planes within a fluorescent sample to create a 3D image with enhanced axial resolution. See Huisken J et al., Optical Sectioning Deep Inside Live Embryos by Selective Plane Illumination Microscopy, *Science* 305:1007-1009 (2004). SPIM, which is limited to only fluorescent imaging, achieves ~6 µm axial resolution in thick samples up to a few millimeters over an FOV ranging between 0.04-2 mm$^2$, which is dictated by either the NA of the objective lens that is used or the active area of the opto-electronic sensor array. In general, these existing optical tomography platforms, as summarized above, all rely on relatively complex and bulky optical setups that are challenging to miniaturize and integrate with microfluidic systems. Therefore, an alternative tomographic microscopy platform which offers both high resolution and a large imaging volume in a compact embodiment may offer an important imaging toolset in various fields including cell and developmental biology, neuroscience and drug discovery.

SUMMARY

In one aspect of the invention, a system and method for lens-free optical tomography is provided that achieves less than 1 µm lateral resolution together with an axial resolution of ~2.5-3 µm over a large FOV of ~14 mm$^2$ as well as an extended DOF of ~4 mm, enabling an on-chip imaging volume of ~15 mm$^3$. This lens-free optical tomography platform merges high resolution in three dimensions (3D) with a significantly large imaging volume, offering a 3D space-bandwidth product that is unmatched by existing optical computed tomography modalities.

In one approach, lens-free tomographic imaging is achieved by rotating a partially coherent light source with ~10 nm spectral bandwidth to illuminate the sample volume from multiple angles (spanning ±50° in air), where at each illumination angle several sub-pixel shifted inline projection holograms of the objects are recorded without using any lenses, lasers or other bulky optical components. The sub-pixel images are then digitally processed to generate a single, high resolution (e.g., pixel super-resolution) hologram of each angular projection. The high resolution holograms are then digitally reconstructed to obtain phase and amplitude information which are then back-projected to compute tomograms of the sample.

Limited spatial and temporal coherence of the hologram recording geometry brings important advantages to the reconstructed images such as reduced speckle and multiple reflection interference noise terms. Furthermore, the unit fringe magnification in the geometry permits recording of inline holograms of the objects even at oblique illumination angles of e.g., >40° which would not be normally feasible with conventional coherent inline holographic imaging schemes that utilize fringe magnification.

In order to minimize the artifacts due to limited angular range of tilted illumination, a dual-axis tomography scheme may be adopted where the light source is rotated along two substantially orthogonal axes. Tomographic imaging performance is quantified using microbeads of different dimensions, as well as by imaging wild type *C. Elegans*. Probing a large volume with good 3D spatial resolution, this lens-free optical tomography platform provides a powerful tool for high-throughput imaging applications in e.g., cell and developmental biology.

In one embodiment, a system for three dimensional imaging of an object contained within a sample includes an image sensor; a sample holder configured to hold the sample, the sample holder disposed adjacent to the image sensor; and an illumination source comprising partially coherent light or coherent light, the illumination source configured to illuminate the sample through at least one of an aperture, fiber-optic cable, or optical waveguide interposed between the illumination source and the sample holder, wherein the illumination source is configured to illuminate the sample through a plurality of different angles.

In another embodiment, a method of obtaining a three dimensional image of an object contained within a sample includes illuminating a sample holder configured to hold the sample with an illumination source emitting partially coherent light or coherent light at a first angle, the light passing through at least one of an aperture or a fiber-optic cable prior to illuminating the sample; illuminating the sample holder with the illumination source emitting light at different angles, the light passing through the aperture or a fiber-optic cable prior to illuminating the sample; obtaining, at each angle, a plurality of sub-pixel image frames from an image sensor disposed on an opposing side of the sample holder; digitally converting the sub-pixel image frames at each angle into a single higher resolution hologram for each angle; digitally reconstructing projection images for each angle from the higher resolution holograms; and digitally back projecting three dimensional tomographic images of the object within the sample.

In still another embodiment, a method of performing three dimensional imaging of an object contained within a sample includes flowing a sample through a flow cell disposed adjacent to an image sensor; illuminating the sample with an illumination source emitting partially coherent light or coherent light at a first angle, the light passing through at least one of an aperture, fiber-optic cable, or optical waveguide prior to illuminating the sample; obtaining a plurality of image frames of the object in the moving sample at the first angle with the image sensor; illuminating the sample with the illumination source at one or more different angles, the light passing through at least one of the aperture, fiber-optic cable, or optical waveguide prior to illuminating the sample; obtaining a plurality of image frames of the object in the moving sample at the one or more different angles with the image sensor; digitally reconstructing a super-resolved projection hologram of the object from the plurality of image frames obtained at the first and one or more different angles; digitally reconstructing complex projection images of the object within the sample based on the super-resolved projection holograms obtained at the first angle and the one or more different angles; and digitally reconstructing three dimensional tomograms of the object within the sample through filtered back-projection of the complex projection images.

In still another embodiment, a portable tomographic imager includes a housing containing a sample holder configured to hold a sample therein; a plurality of partially coherent or coherent light sources disposed in the housing at varying angles with respect to a first side of the sample, each of the plurality of light sources being coupled to respective waveguides; a microcontroller operatively connected to the plurality of light sources, the microcontroller configured to selectively activate individual light sources; an electromagnetic actuator configured to move the waveguides in substantially orthogonal directions; and an image sensor disposed in the housing on a second opposing side of the sample.

In another embodiment a portable tomographic imager includes a housing containing a sample holder configured to hold a sample therein; a plurality of partially coherent or coherent light sources disposed in the housing at varying angles with respect to a first side of the sample, each of the plurality of light sources being coupled to respective spatial apertures; a microcontroller operatively connected to the plurality of light sources, the microcontroller configured to selectively activate individual light sources; an electromagnetic actuator configured to move the spatial apertures in substantially orthogonal directions; and an image sensor disposed in the housing on a second opposing side of the sample.

BRIEF DESCRIPTION OF THE DRAWINGS

FIG. 9A illustrates a holographically recorded projection image (pixel super-resolved hologram of 10 μm beads) at an angle of 0°. The beads are distributed at different layers within a thick multi-layer sample. Arrows with different sizes in FIG. 9A point to beads located at different layers within the multilayer chamber.

FIGS. 9B-9E illustrate tomograms for different depths within the chamber (FIG. 9B: z=3.97 mm; FIG. 9C: z=1.740 mm; FIG. 9D: z=730 μm; FIG. 9E: z=742 μm). Tomograms were obtained with dual-axis imaging.

FIG. 10C does not exhibit any spurious details, which reveals that the digital extraction process does not introduce artifacts to measured data.

FIG. 13A illustrates the tomographic optofluidic image of *C. Elegans* at a depth slice of −6 μm. The scale bar is 50 μm in length.

FIG. 13B illustrates the tomographic optofluidic image of *C. Elegans* at a depth slice of −3 μm. The scale bar is 50 μm in length.

FIG. 13C illustrates the tomographic optofluidic image of *C. Elegans* at a depth slice of 0 μm. The scale bar is 50 μm in length.

FIG. 13D illustrates the tomographic optofluidic image of *C. Elegans* at a depth slice of +3 μm. The scale bar is 50 μm in length.

FIG. 13E illustrates the tomographic optofluidic image of C. Elegans at a depth slice of +6 µm. The scale bar is 50 µm in length.

FIG. 13F illustrates a 10× microscope image of C. Elegans for comparison purposes.

FIG. 15A is a low resolution (LR) vertical projection hologram for a 2 µm diameter micro-particle.

FIG. 15B is a digitally synthesized pixel super-resolved (SR) hologram for the same particle, where holographic fringes with much higher frequencies can be observed, that are normally undersampled in FIG. 15A.

FIG. 15C illustrates the reconstructed image of the same micro-particle in x-y plane using the LR hologram shown in FIG. 15A.

FIG. 15D illustrates the reconstructed image of the micro-particle in x-y plane using SR hologram shown in FIG. 15B.

FIG. 15E illustrates the y-z and x-z cross sections for the micro-particle obtained by reconstructing the LR hologram in FIG. 15A.

FIG. 15F illustrates the y-z and x-z cross sections for the same micro-particle obtained by reconstructing the SR hologram in FIG. 15B.

FIGS. 16A-16C illustrate the sectional images (tomograms) through the center of the micro-particle in y-z, x-z and x-y planes, respectively.

FIG. 17A illustrates the lensfree computed tomogram of a chamber filled with randomly distributed micro-beads with 5 µm diameter at a depth of −7 µm. The arrows in each images show the beads that are in-focus at a given depth.

FIG. 17B illustrates the lensfree computed tomogram of a chamber filled with randomly distributed micro-beads with 5 µm diameter at a depth of 0 µm. The arrows in each images show the beads that are in-focus at a given depth.

FIG. 17C illustrates the lensfree computed tomogram of a chamber filled with randomly distributed micro-beads with 5 µm diameter at a depth of +7 µm. The arrows in each images show the beads that are in-focus at a given depth.

FIG. 17D illustrates the lensfree computed tomogram of a chamber filled with randomly distributed micro-beads with 5 µm diameter at a depth of 16 µm. The arrows in each images show the beads that are in-focus at a given depth. The inset in FIG. 17D enclosed with the dashed rectangle shows sectioning of two axially overlapping micro-beads, shown by the dashed circles in FIG. 17F and FIG. 17E, both by lensfree tomography and conventional microscopy (40×, 0.65-NA), respectively.

FIG. 17E illustrates the lensfree computed tomogram of a chamber filled with randomly distributed micro-beads with 5 µm diameter at a depth of 32 µm. The arrows in each images show the beads that are in-focus at a given depth.

FIG. 17F-17J illustrate microscope images (40×, 0.65-NA) for depths corresponding to those of FIGS. 17A-17E.

FIG. 18A illustrates a zoomed tomographic image through the center of an arbitrary bead together with its line profiles along x and y.

FIG. 18B illustrates the axial line profile and its derivative for the same bead as in FIG. 18A, suggesting an axial resolution of ~6 µm.

FIG. 19A illustrates a recorded hologram (angle of 0°) for a multilayer chamber (mounted with 0.7 mm elevation above the sensor) of 10 µm beads, suspended over 4 layers with a total thickness of ~3.5 mm using the hand-held imager. The holograms of beads at different depths are visible (with varying sizes as a function of the distance from the sensor-chip).

FIG. 19B illustrates the computed tomographic image at a depth of 719 µm.

FIG. 19C illustrates the computed tomographic image at a depth of 750 µm.

FIG. 19D illustrates the computed tomographic image at a depth of 1840 µm.

FIG. 19E illustrates the computed tomographic image at a depth of 1851 µm.

FIG. 19F illustrates the computed tomographic image at a depth of 4225 µm.

FIG. 19G illustrates a digitally cleaned hologram of FIG. 19A whereby objects only in a selected layer (z~0.75 mm) is illustrated.

FIG. 19H illustrates a digitally cleaned hologram of FIG. 19A whereby objects only in a selected layer (z~1.8 mm) is illustrated.

FIG. 19I illustrates a digitally cleaned hologram of FIG. 19A whereby objects only in a selected layer (z~4.2 mm) is illustrated.

FIG. 20A illustrates computed tomographic images for different depths of a H. Nana egg obtained using the hand held device. Depths include −8 µm (a1); 0 (a2); and +6 µm (a3).

FIG. 20B illustrates 40× microscope images of the H. Nana egg at the same depths illustrated in FIG. 20A.

DETAILED DESCRIPTION OF THE ILLUSTRATED EMBODIMENTS

Figure 1A:
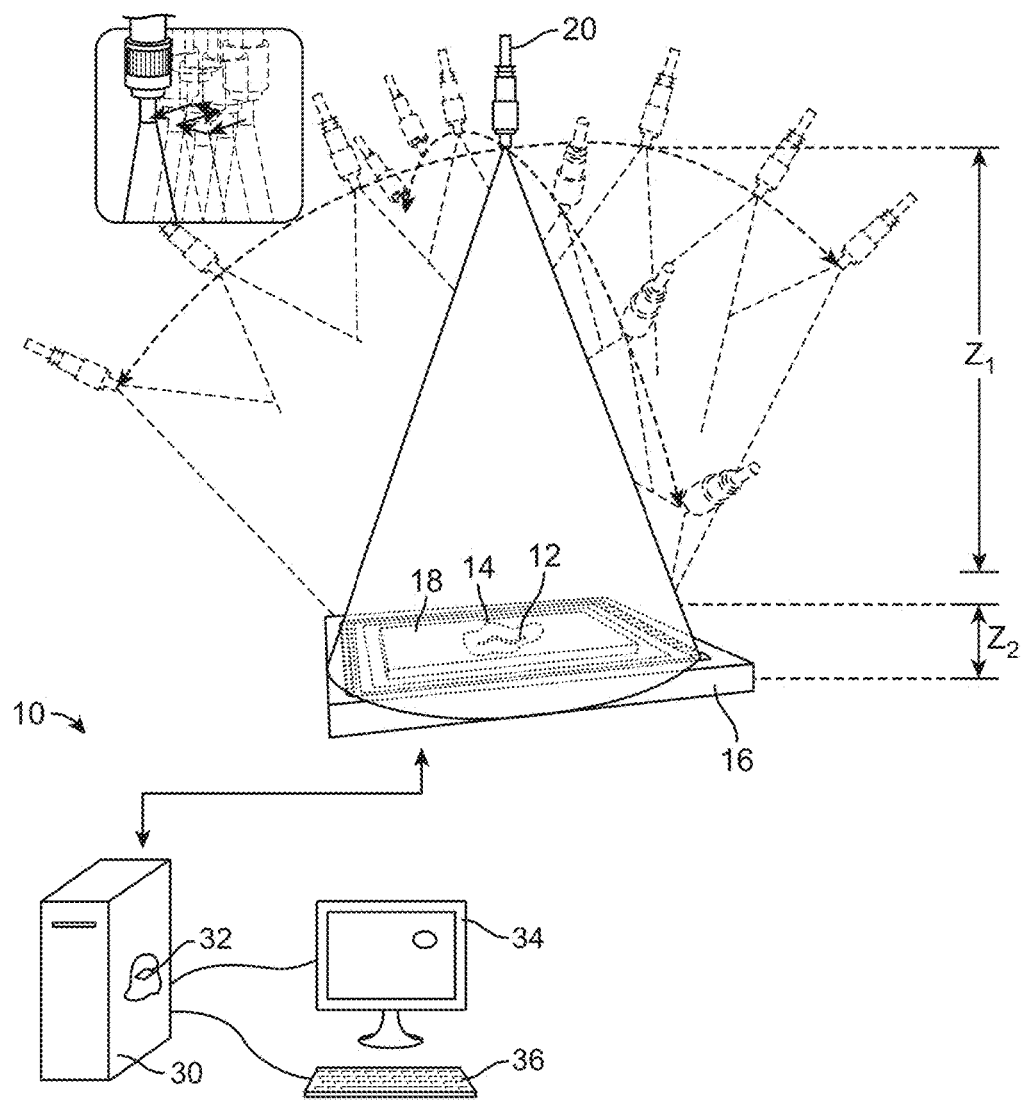
FIG. 1A illustrates a system according to one embodiment for the tomographic imaging of one or more objects within a sample.
Figure 1B:
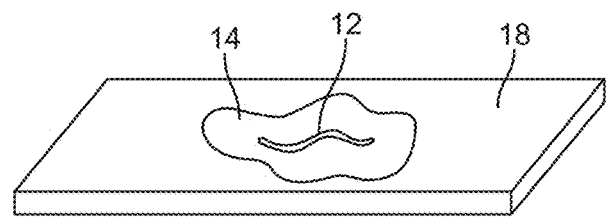
FIG. 1B illustrates a sample holder containing a sample with an object located herein.

FIG. 1A illustrates a system 10 for tomographic imaging of an object 12 within a sample 14 (best seen in FIG. 1B). The object 12 may include a cell or biological component or constituent (e.g., a cellular organelle or substructure). The object 12 may even include a multicellular organism or the like. Alternatively, the object 12 may be a particle or other object. FIG. 1A illustrates an object 12 to be imaged that is disposed some distance above an image sensor 16. In some embodiments, the sample 14 containing one or more objects 12 is placed directly atop an optically transparent cover or surface of the image sensor 16 (e.g., glass cover). Alternatively, the sample 14 containing one or more objects 12 is placed on an optically transparent sample holder 18 such as a glass or plastic slide, coverslip, or the like as seen in FIG. 1B.

Regardless, the surface of image sensor 16 may be in contact with or close proximity to the sample 14. Generally, the object 12 within the sample 14 is several millimeters within the active surface of the image sensor 16. The image sensor 16 may include, for example, a charged coupled device (CCD) or a complementary metal-oxide semiconductor (CMOS) device. The image sensor 16 may be monochromatic or color. The image sensor 16 generally has a small pixel size which is less than 9.0 µm in size and more particularly, smaller than 5.0 µm in size (e.g., 2.2 µm or smaller). Generally, image sensors 16 having smaller pixel size will produce higher resolutions. One benefit of the imaging method described herein is that a spatial resolution better than pixel size can be obtained.

Still referring to FIG. 1A, the system 10 includes an illumination source 20 that is configured to illuminate a first side (top side as seen in FIG. 1A) of the sample holder 18. The illumination source 20 is preferably a spatially coherent or a partially coherent light source. Light emitting diodes (LEDs) are one example of an illumination source 20. LEDs are relative inexpensive, durable, and have generally low power requirements. Of course, other light sources may also be used such as a Xenon lamp with a filter. A light bulb is also an option as the illumination source 20. A coherent beam of light such as a laser may also be used (e.g., laser diode). The illumination source 20 preferably has a spectral bandwidth that is between about 0.1 and about 100 nm, although the spectral bandwidth may be even smaller or larger. Further, the illumination source 20 may include at least partially coherent light having a spatial coherence diameter between about 0.1 to 10,000 µm.

Figure 1C:
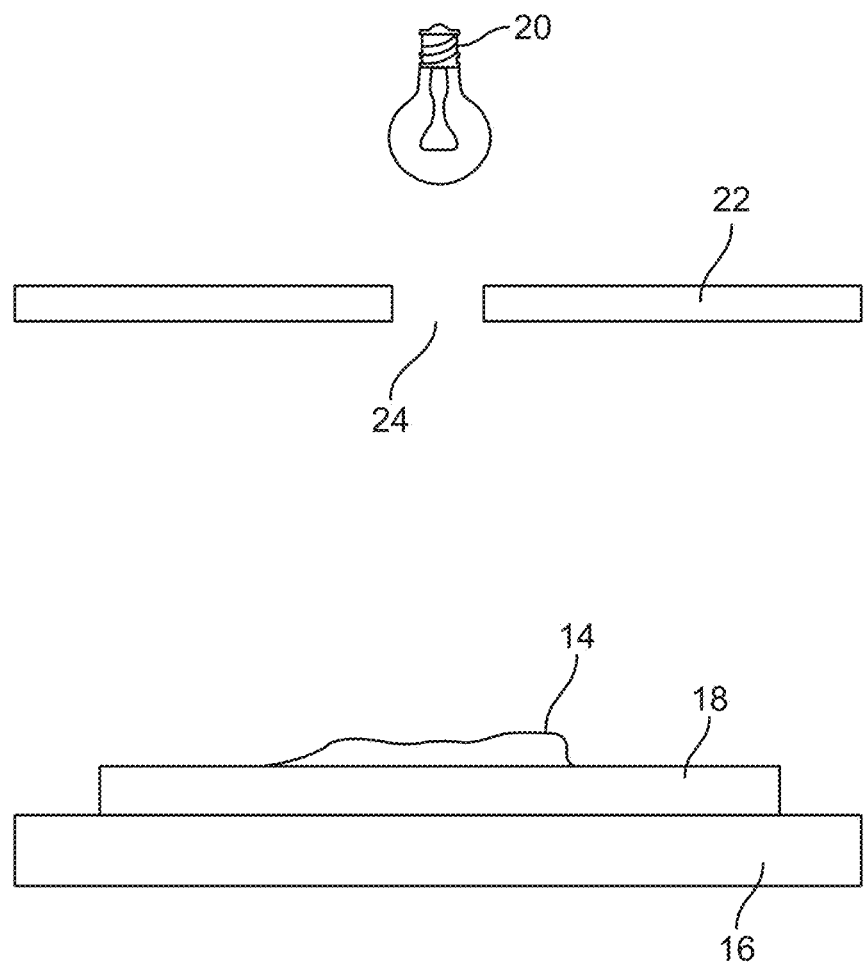
FIG. 1C illustrates the orientation of a spatial filter including an aperture therein that may optionally be interposed between the illumination source and the sample containing the object(s).

With reference to FIG. 1C, a spatial filter 22 may be optionally interposed between the illumination source 20 and the sample 14 containing the object(s) 12. The spatial filter 22 includes an opaque surface that has an aperture 24 contained therein that is configured to permit the passage of illumination (e.g., spatial aperture or pinhole). The aperture 24 has a diameter (D) that is typically in the range of 50 µm to about 100 µm. Alternatively, the spatial filter 22 may be integrated into the distal end of the illumination source 20 as illustrated in FIG. 1A. For example, the illumination source 20 may be coupled to an optical fiber as seen in FIG. 1A or another optical waveguide. With respect to the optical fiber, the fiber includes an inner core with a higher refractive index than the outer surface so that light is guided therein. In this embodiment, there is no need for a separate opaque surface with an aperture 24. Instead, the optical fiber itself operates as the spatial filter 22. In this embodiment, the core of the optical fiber may have a diameter within the same range the aperture 24 described herein. As seen in FIG. 1A, the distal end (spatial filter 22) of the fiber optic cable illumination source 20 is located at a distance $z_1$ from the sample holder 18 (or sample 14). The imaging plane of the image sensor 16 is located at a distance $z_2$ from the sample holder 18 (or sample 14). In the system 10 described herein, $z_2 \ll z_1$. For example, the distance $z_1$ may be on the order of around 1 cm to around 10 cm. In other embodiments, the range may be smaller, for example, between around 5 cm to around 10 cm. The distance $z_2$ may be on the order of around 0.05 mm to 2 cm, however, in other embodiments this distance $z_2$ may be between around 1 mm to 2 mm. In the system 10, the propagation distance $z_1$ is such that it allows for spatial coherence to develop at the plane of the object 12, and light scattered by the object 12 interferes with background light to form a lens-free in-line hologram on the image sensor 16.

Still referring to FIG. 1A, the system 10 includes a computer 30 such as a laptop, desktop, or the like that is operatively connected to the system 10 such that lower resolution images (e.g., lower resolution or raw image frames) are transferred from the image sensor 16 to the computer 30 for data acquisition and image processing. The computer 30 includes one or more processors 32 that, as described herein in more detail, runs or executes software that takes multiple, sub-pixel (low resolution) images taken at one angle and creates a single, high resolution projection hologram image of the objects 12. The software also digitally reconstructs complex projection images of the objects 12 that includes both amplitude and phase information. Having both the holographic amplitude and recovered phase of the same image, the software then digitally reconstructs three dimensional tomograms of the object(s) 12 through filtered back-propagation of the complex projection images. The reconstructed tomographic images can be displayed to the user on, for example, a display 34 or the like. The user may, for example, interface with the computer 30 via an input device 36 such as a keyboard or mouse to select different tomographic imaging planes.

FIG. 1A illustrates first and second arcs 40, 42 that are substantially orthogonal to one another. The first and second arcs 40, 42 represents various angles at which the illumination source 20 illuminates the objects 12 contained in the sample 14. Various imaging locations (shown in phantom) are illustrated along the first and second arcs 40, 42. Generally, the illumination source 20 is moved at angles ranging from −89° to +89° with top-dead center above the image sensor 16 (as seen in FIG. 1A) representing the 0° position. In one embodiment, the illumination source 20 is moved along one of the arcs 40, 42 relative to a stationary imaging sensor 16. Alternatively, the illumination source 20 may remain stationary while the imaging sensor 16 moves to create the same angled illumination. In still another alternative, both the illumination source 20 and the image sensor 16 may move relative to one another. Generally, it is preferred to move the illumination source 20 as opposed to the image sensor 16 having the sample 14 therein as it tends to disturb the objects 12 contained within the sample 14. The illumination source 20 and/or image sensor 16 may be moved by any number of mechanical actuator including a mechanical stage, arm, slide, or the like that moves the illumination source 20 at various angles with respect to the image sensor 16.

Still referring to FIG. 1A, the illumination source 20 also has the ability to move, at each angle along the arcs 40, 42 in a plane that is substantially parallel with the imaging plane. The inset image of FIG. 1A illustrates two-dimensional (e.g., x and y displacement) movement of the illumination source 20 in a snake-like pattern. In this manner, the illumination source 20 is able to make relatively small displacement jogs (e.g., less than 70 µm). As explained below, the small discrete shifts parallel to the image sensor 16 are used to generate a single, high resolution image (e.g., pixel super-resolution). For example, a 3×3 grid may be used to obtain nine (9) different low resolution (LR) images in the x-y plane at each angle location on the arcs 40, 42. With reference to FIG. 1C, as an alternative to moving the illumination source 20, the aperture 24 may be moved relative to a stationary illumination source 20. Any number of mechanical actuators may be used including, for example, a stepper motor, moveable stage, piezoelectric element, or solenoid.

While FIG. 1A illustrates arcs 40, 42 that are positioned substantially orthogonal to one another. In other embodiments, it the illumination source 20 may be positioned at different angles on a three dimensional surface such as a sphere or ellipsoid. The objects 12 are generally located close to the center of the three dimensional surface defined by the shape (e.g., centroid). In this embodiment, the illumination source 20 may trace portions of a three dimensional surface as opposed to two perpendicular arcs.

Figure 2:
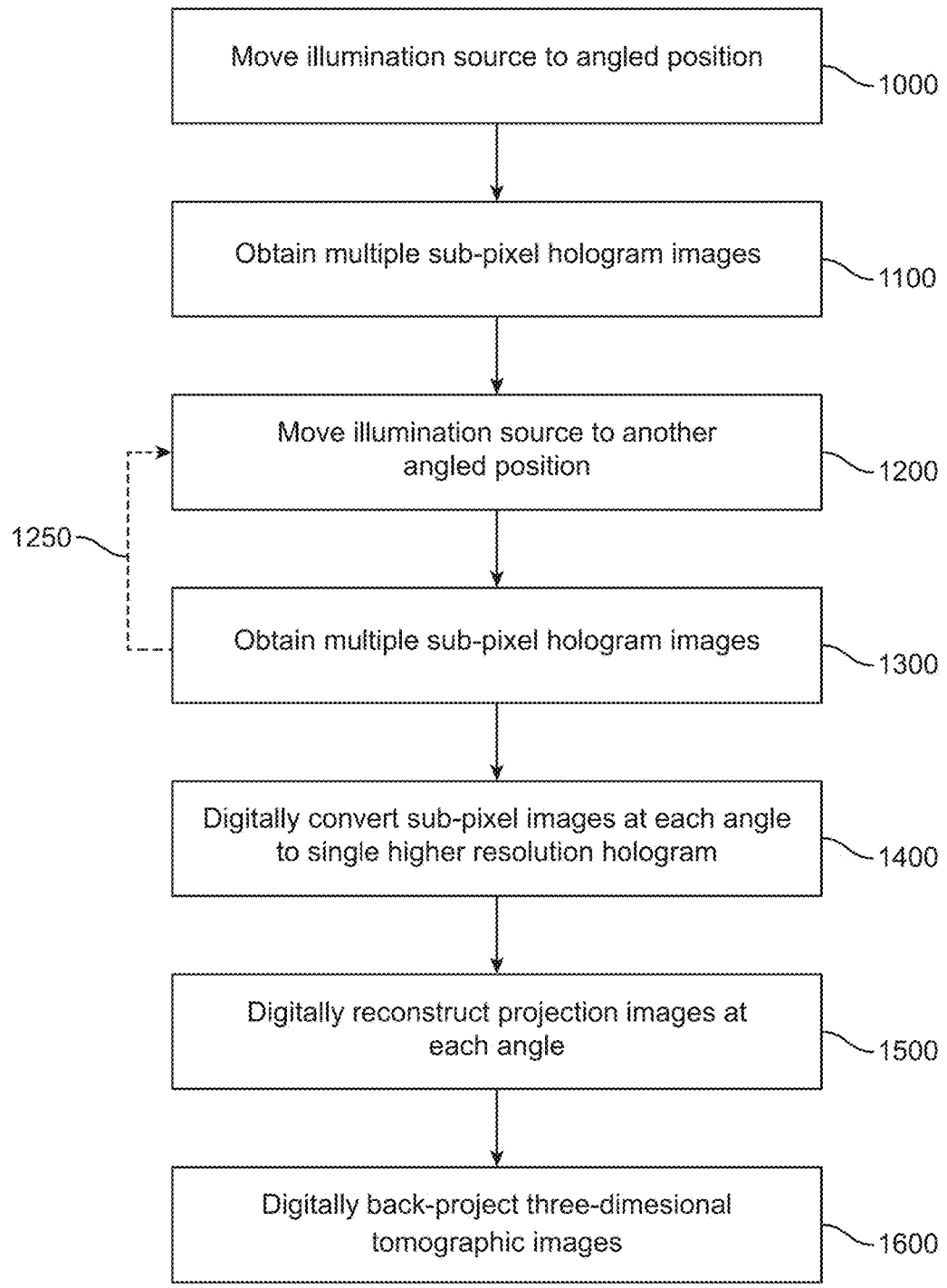
FIG. 2 illustrates a top-level flowchart of how the system obtains three dimensional tomographic images of objects within a sample.

FIG. 2 illustrates a top-level flowchart of how the system 10 obtains three dimensional tomographic images of objects 12 within a sample 14. After samples 14 are loaded into the sample holder 18, the illumination source 20 is moved to a first angled position as seen in operation 1000. The illumination source 10 illuminates the sample 14 and multiple sub-pixel (LR) hologram images are obtained as seen in operation 1100. In this step, according to one embodiment, multiple sub-pixel images are obtained by moving the illumination source 10 in a plane generally parallel to the image sensor 16 (e.g., x and y plane). This movement occurs while the illumination source 10 is at the first angled position. For example, nine (9) images taken in a 3×3 array may be taken at the first angled location. Next, as seen in operation 1200, the illumination source 10 is moved to another angled position. At this different angled position, the illumination source 10 illuminates the sample 14 and multiple sub-pixel hologram images are obtained as seen in operation 1300. In this step, multiple sub-pixel images are again obtained by moving the illumination source 10 in a plane generally parallel to the image sensor 16 (e.g., x and y plane). The illumination source 20 may then be moved again to another angled position where multiple sub-pixel holograms are obtained as seen in operation 1250. This process may repeat itself any number of times so that images are obtained at a number of different angles. For example, multiple sub-pixel hologram images may be taken along arcs 40, 42.

In operation 1400, the multiple sub-pixel images at each angle are digitally converted to a single, higher resolution hologram (SR hologram), using a pixel super-resolution technique, the details of which are disclosed in Bishara et al., Lensfree on-chip microscopy over a wide field-of-view using pixel super-resolution, *Optics Express* 18:11181-11191 (2010), which is incorporated by reference. First, the shifts between these holograms are estimated with a local-gradient based iterative algorithm. Once the shifts are estimated, a high resolution grid is iteratively calculated, which is compatible with all the measured shifted holograms. In these iterations, the cost function to minimize is chosen as the mean square error between the down-sampled versions of the high-resolution hologram and the corresponding sub-pixel shifted raw holograms.

Next, in operation 1500, complex projection images are digitally reconstructed at each angle. Digitally synthesized super-resolved holographic projections are reconstructed to obtain the lens-free projection images of the objects at various illumination angles. It should be emphasized that the holograms recorded with oblique illumination angles are still in-line holograms due to co-axial propagation of the scattered object wave and the unperturbed reference wave toward the sensor array. Consequently, digitally reconstructed images are contaminated by the twin-image artifact, which is a manifestation of the fact that the phase of the complex field in the detector plane is lost during the recording process. In order to obtain faithful projection images, a size-constrained iterative phase recovery algorithm is utilized, which enables recovering the phase of the complex field detected by the sensor. Details regarding the phase recover algorithm may be found in Mudanyali et al., Compact, Light-weight and Cost-effective Microscope based on Lensless Incoherent Holography for Telemedicine Applications, *Lab Chip* 10:1417-1428 (2010), which is incorporated by reference as if set forth fully herein.

Similar to the conventional vertical illumination case, holograms recorded with oblique illumination angles are multiplied with a reference wave that is the digital replica of the reference wave utilized for recording the holograms, which translates to using a plane reference wave tilted with respect to sensor normal. It should be noted that the tilt angle of this reconstruction wave is not equal to the tilt of the illuminating beam, due to refraction of light in the sample holder. In fact, the digital reconstruction angle for projection holograms are determined by calculating the inverse tangent of the ratio $\Delta d/z_2$, where $\Delta d$ denotes the lateral shifts of the holograms of objects with respect to their positions in the vertical projection image, and $z_2$ is either experimentally known, or is iteratively determined by the digital reconstruction distance of the vertical hologram.

For iterative phase recovery, the complex field is digitally propagated back and forth between the parallel image detector and object planes. In order to obtain the projection image in the plane normal to the illumination, the recovered field is also interpolated on a grid whose dimension along the tilt direction is rescaled by $\cos(\theta)$, where $\theta$ is the angle of digital reconstruction. In addition, the projection images need to be aligned with respect to a common center-of-rotation before computing the tomograms. To achieve that, an automated two-step cross-correlation was implemented based image registration algorithm. Since the projection images obtained with successive illumination angles (e.g., 50° and 48°) are very similar to each other, the first step of image-registration is performed by cross-correlating the projection images obtained at adjacent angles. In most cases, especially when the object is a large connected structure such as *C. Elegans*, this step yields a successfully registered set of projections. However, if the FOV contains distributed small objects such as beads, the slight differences in projection images due to perspective change, even for adjacent angles, may deteriorate the registration accuracy. In this case the bead at the center of the projection images, which is also assumed to be the center-of-rotation, walks off the center of projection images, indicating poor image registration. Then, a second step of registration is utilized following the first one, where the bead at the center of the vertical projection image is used as a global reference, and all other projection images are automatically aligned with respect to that particular bead. Since the reference bead is already roughly aligned in the first step, the second correlation step is performed only on the reference bead by correlating cropped projection images with the cropped global, i.e. vertical, projection image.

The large $z_1/z_2$ ratio in this lens-free recording scheme permits a detection NA that is close to the refractive index of the medium. While this property of the system is of paramount importance for recording holograms with tilted illumination beams, the design of the opto-electronic sensor arrays limits the maximum angle that we can utilize. Opto-electronic sensor arrays in general are designed for lens-based imaging systems, where the angle of incident rays does not typically exceed 20°-30°, as a result of which holograms recorded at illumination angles larger than ±50° start to exhibit artifacts. For this reason, experimental projection holograms were obtained within a limited angular range of −50° to +50°, along two different rotation axes. It should be understood, however, that the angular range may be larger than this, for example, spanning angles between −89° and +89°, or in some instances spanning angles between −89° and +89°

The lens-free projection images (both phase and amplitude) are subject to a filtered back-projection algorithm to produce three-dimensional images as seen in operation 1600. Fourier-projection theorem allows reconstructing the 3D transmission function of an object from its 2D projections along different directions. Details regarding the back-projection method may be found in Radermacher M., Weighted back-projection methods, Electron Tomography: Methods for three dimensional visualization of structures in the cell, (Springer, New York, $2^{nd}$ ed.) pp. 245-273 (2006), which is incorporated herein by reference. Of course, other tomographic reconstruction methods known to those skilled in the art may be used as well.

Accordingly, one pixel super-resolved (SR) hologram for each illumination angle is digitally synthesized by utilizing multiple sub-pixel (LR) shifted holograms, which is followed by holographic reconstruction of all high resolution holograms yielding lens-free projection images. Then, in operation 1600, these reconstructed lens-free projection images (both phase and amplitude) are used to compute 3D tomograms of micro-objects using a filtered back-projection algorithm. A fundamental requirement for this technique, commonly referred to as the projection assumption, is that the projection images should represent a linear summation of a certain property of the object, for which tomograms can be computed. While it is much easier to satisfy this condition in X-Ray Computed Tomography due to negligible diffraction at that part of the electromagnetic spectrum, computed tomography in the optical regime requires weakly scattering objects. Similarly, this lens-free optical tomography modality also requires that the majority of the photons experience at most a single scattering event over the volume of each stack of tomograms. For weakly scattering objects, together with the long depth-of-focus of the system, complex scattering potential becomes additive along the direction of illumination. Consequently, tomograms of complex scattering potential of an object can be computed by applying a filtered back-projection algorithm whose inputs are the complex projection images calculated by holographic reconstruction of pixel super-resolved lens-free holograms at each illumination angle.

Since holograms are recorded for a limited angular range of ±50°, there is a missing region in the Fourier space of the object, commonly known as the missing wedge. The main implication of the missing wedge is reduced axial resolution, which limits the axial resolution to a value larger than the lateral. Further, in the lateral plane, ringing artifacts are observed as well as narrowing of the point-spread function (PSF) along the direction of rotation of the illumination such that the PSF in the x-y plane becomes elliptical.

In order to minimize these imaging artifacts, a dual-axis tomography scheme is used. Projection images obtained along each tilt direction are separately back-projected to compute two sets of complex tomograms. These tomograms are merged in Fourier space following the sequence given in Mastronarde D. N., Dual-Axis Tomography: An Approach with Alignment Methods That Preserve Resolution, Journal of Structural Biology 120:343-352 (1997), which is incorporated by reference as if set forth fully herein. Accordingly, the regions where both sets of tomograms have data for are averaged, while regions where only one set has useful data in its Fourier space, are filled by the data of the corresponding tomograms. As a result, the missing wedge is minimized to a missing pyramid, significantly reducing the aforementioned limited angle tomography artifacts. To further reduce the artifacts outside the support of the object, a mask is applied that is utilized for digital reconstruction of the vertical projection hologram to all tomograms. The missing wedge could also be iteratively filled to improve resolution and reduce artifacts by implementing iterative constraint algorithms based on a priori information of the 3D support or transmission function of the object.

Figure 3:
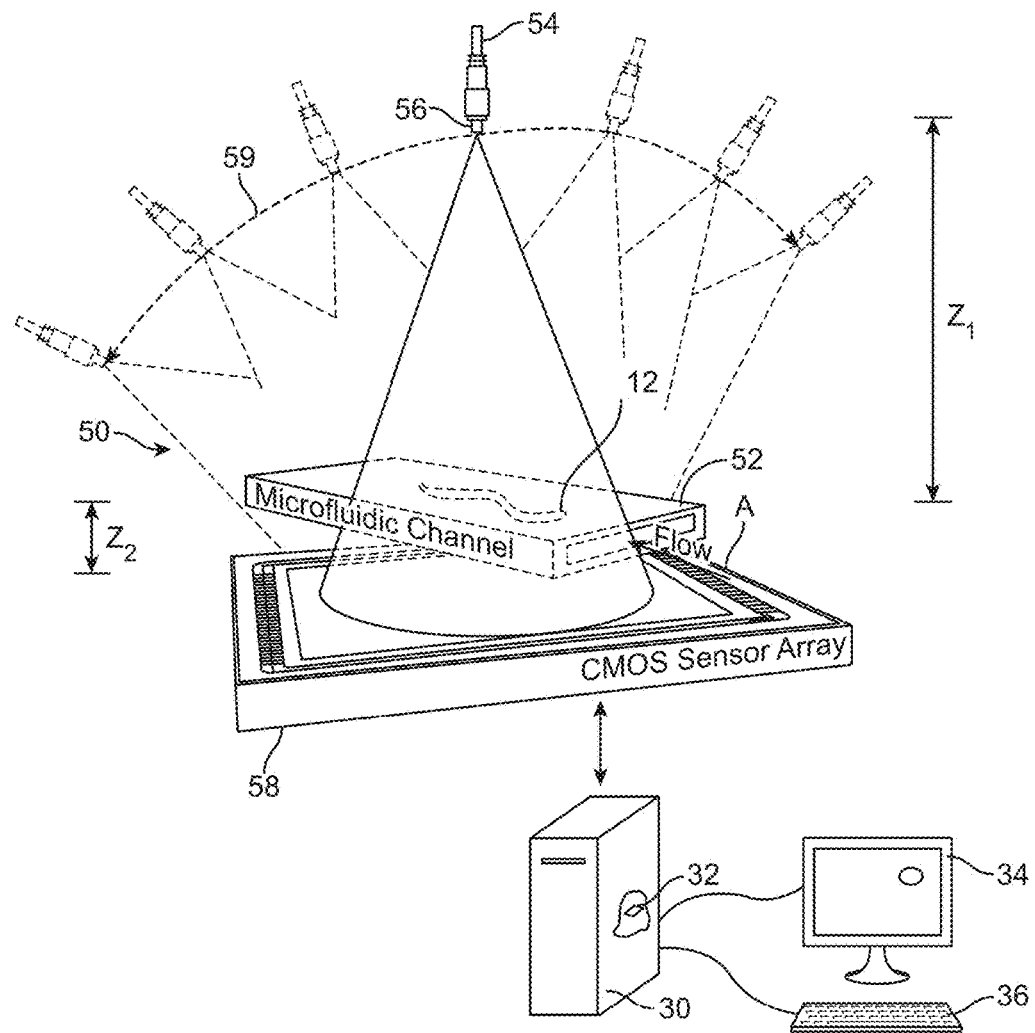
FIG. 3 illustrates a system according to another embodiment for the tomographic imaging of one or more objects within a sample. In this embodiment, the sample is flowing through a flow cell.

FIG. 3 illustrates another embodiment of a system 50 for the tomographic imaging of an object 12 within a sample 14. In this embodiment, the object is seen as a worm, e.g., *C. Elegans* while the sample is a 14 flowing sample volume. The system 50 includes a flow cell 52 that is configured to carry the moving object 12 within a flow of a carrier fluid.

In one aspect, the moving object 12 may include a cell or other biological component. The moving object 12 may also include a non-biological particle or the like. The carrier fluid is typically a liquid in which the moving object resides. The carrier fluid could also be a gas in some circumstances. When the moving object 12 is a cell, the carrier fluid is typically a physiological compatible buffer solution or the like (e.g., phosphate buffered saline). The flow cell 42 is a substantially straight, three-dimensional conduit that is substantially optically transparent (at least with respect to source of illumination described in more detail herein). The flow cell 52 may be made from glass, plastic, or other materials commonly used in connection with microfluidic devices. The conduit of the flow cell 52 may have a regularly-shaped cross-sectional area such as a square or rectangle. The internal dimensions of the flow cell 52 that contain the moving object 12 may vary. For example, the flow cell 52 may have heights/widths that are on the millimeter scale. Alternatively, the flow cell 52 may have heights/widths that are on the micrometer scale. In this regard, the flow cell 52 may include a microchannel or the like.

The moving objects 12 are moved or flowed through the flow cell 52 using one or more pumping techniques. For example, a pressure gradient may be established to pump fluid containing objects 12 within flow cell 52. Alternatively, the moving objects 12 may be moved through the flow cell 52 using electro-kinetic motion with electrodes at opposing ends of the flow cell 52 being used. In this regard, any particular pumping modality may be used to move the objects 12 through the flow cell 52. Examples include the use of pumps like syringe pumps, dielectrophoresis based electrodes, magnetohydrodynamic electrodes, and the like.

Still referring to FIG. 3, the system 50 includes an illumination source 54 that is configured to illuminate a first side (top side as seen in FIG. 3) of the flow cell 52. The illumination source 54 is preferably a spatially coherent or a partially coherent light source. Light emitting diodes (LEDs) are one example of an illumination source 54. LEDs are relative inexpensive, durable, and have generally low power requirements. Of course, other light sources may also be used such as a Xenon lamp with a filter. A laser or a light bulb are also options as the illumination source 54. The illumination source 54 preferably has a spectral bandwidth that is between about 0.1 and about 100 nm, although the spectral bandwidth may be even smaller or larger. Further, the illumination source 54 may include at least partially coherent light having a spatial coherence diameter between about 0.1 to 10,000 µm.

A spatial filter 56 may be integrated into the distal end of the illumination source 54 as illustrated in FIG. 3. For example, the illumination source 54 may be coupled to an optical fiber as seen in FIG. 3 or another optical waveguide. With respect to the optical fiber, the fiber includes an inner core with a higher refractive index than the outer surface so that light is guided therein. Alternatively, the spatial filter 56 may include an opaque surface with an aperture 24 like that illustrated in FIG. 1C. The spatial filter 56 serves to make the light more coherent.

As seen in FIG. 3, an image sensor 58 is disposed on a second, opposite side of the flow cell 52 such that the flow cell 52 is interposed between the illumination source 54 and the image sensor 58. The image sensor 58 is located adjacent to the back side of the flow cell 52. The surface of image sensor 58 may be in contact with or close proximity to the back side of the flow cell 52. For example, the flow cell 52 may be placed directly atop the glass or other optically transparent layer that typically covers the image sensor 58.

The image sensor 58 may include, for example, a charged coupled device (CCD) or a complementary metal-oxide semiconductor (CMOS) device. The image sensor 58 may be monochromatic or color. The image sensor 58 generally has a small pixel size which is less than 9.0 µm in size and more particularly, smaller than 5.0 µm in size (e.g., 2.2 µm or smaller). Generally, image sensors 58 having smaller pixel size will produce higher resolutions.

Still referring to FIG. 3, the illumination source 54 is located at a distance $z_1$ from the flow cell 52. The imaging plane of the image sensor 58 is located at a distance $z_2$ from the flow cell 52. In the system 50 described herein, $z_2 \ll z_1$. For example, the distance $z_1$ may be on the order of around 1 cm to around 10 cm. In other embodiments, the range may be smaller, for example, between around 5 cm to around 10 cm. The distance $z_2$ may be on the order of around 0.05 mm to 2 cm, however, in other embodiments this distance $z_2$ may be between around 1 mm to 2 mm. In the system 50, the propagation distance $z_1$ is such that it allows for spatial coherence to develop at the plane of the moving object 12, and light scattered by the moving object 12 interferes with background light to form a lens-free in-line hologram on the image sensor 58.

As seen in FIG. 3, the moving objects 12 flow within the flow cell 52 in the direction of arrow A. Arrow A is substantially parallel with the long axis of the flow cell 52. The direction of flow A (and thus the flow cell 52) is slightly angled relative to the image sensor 58. The exact value of this angle is not critical and need not be known a priori; it simply ensures that the flow of the moving object 12 along the flow cell 52 will generate a shift component in both axes directions, x and y of the image sensor 22. The angle should generally be between a non-zero angle and less than 45°. As in the prior embodiment illustrated in FIG. 1A, the illumination source 54 is moveable to illuminate the flow cell 52 at different angles.

Still referring to FIG. 3, the system 50 includes a computer 30 such as a laptop, desktop, or the like that is operatively connected to the system 50 such that lower resolution images (e.g., lower resolution or raw image frames) are transferred from the image sensor 58 to the computer 30 for data acquisition and image processing. The computer 30 includes one or more processors 32 that, as described herein in more detail, runs or executes software that acquires an image of the moving object(s) 12 that includes the holographic amplitude or intensity. The software on the computer 30 then recovers the lost phase of the image. Having both the holographic amplitude and recovered phase of the same image, the software then reconstructs a higher resolution image of the moving object(s) 12. This reconstructed image can be displayed to the user on, for example, a display 34 or the like. The software may also identify and display particular cells of interest based on their holographic signature.

Moving objects 12 that flow through the flow cell 52 are imaged using the image sensor 58. In particular, a plurality of low resolution holographic image frames is acquired using the angularly offset image sensor 58. Because of the unit fringe magnification of the system imaging geometry, depending on the pixel size at the image sensor 58, the acquired holograms may be under-sampled. On the other hand, since during the flow each lens-free object hologram is sampled with different sub-pixel shifts as a function of time, one can use a pixel super-resolution algorithm to digitally synthesize a high-resolution hologram that has an effective pixel size of e.g., <0.5 µm, which is significantly smaller than the physical pixel size of the sensor (e.g., >2 µm). Thus, the system 50 uses the flow of the moving object 12 within the flow cell 52 to digitally create smaller pixels for hologram sampling. Such a super-resolved digital in-line hologram, after elimination of the twin-image artifact, enables high-resolution lens-free imaging of the moving objects 12.

FIG. 3 illustrates an arc 59 along which the illumination source 54 may move to image the flow cell 52 from different angles. Various imaging locations (shown in phantom) are illustrated along the arc 59. Generally, the illumination source 54 is moved at angles ranging from −89° to +89° with top-dead center above the image sensor 58 (as seen in FIG. 3) representing the 0° position. The system 50 further includes a computer 30 having at least one processor 32 therein that is used to execute software for the processing and analysis of images as in the prior embodiment. A monitor 34 and input device 36 may be connected to the computer 30 for displaying results and interfacing with the computer 30.

The embodiment of FIG. 3 operates in the same manner as described in FIG. 2. The difference being that in operation 1100 there is no need to move the illumination source 54 in the x-y direction in a plane that is parallel to the image sensor 58. This operation is not needed due to the flowing object 12 which itself provides the shift in the holograms of the objects 12.

Figure 4:
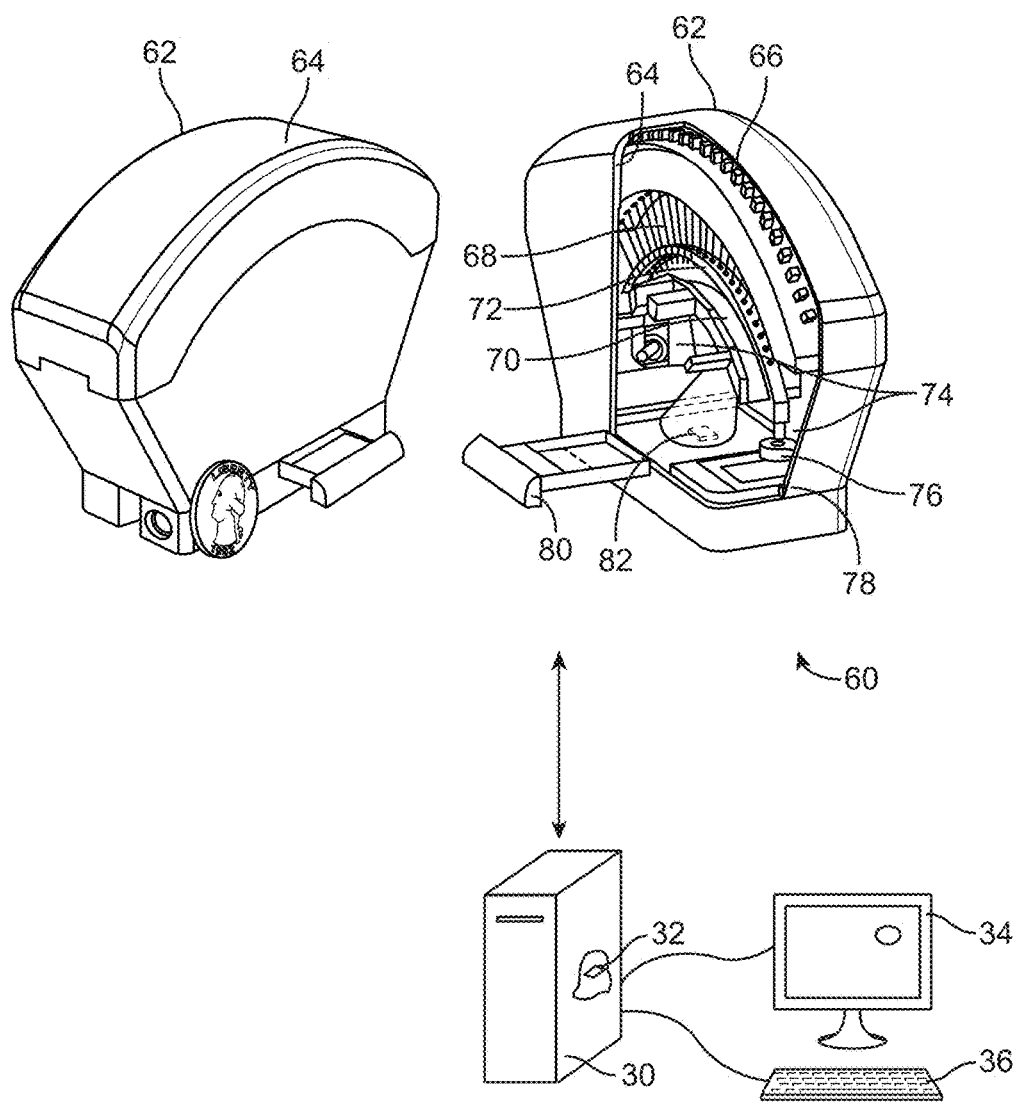
FIG. 4 illustrates a system according to another embodiment for the tomographic imaging of one or more objects within a sample. In this embodiment, the system includes a hand-held or portable imager.

FIG. 4 illustrates another embodiment of a system 60 for the tomographic imaging of an object 12 within a sample 14. In this embodiment, the system 60 includes a hand-held or portable imager 62 that includes a housing 64. The housing 64 may be made from a rugged plastic or metal material and is used to contained or otherwise house the various components of the portable imager 62. The housing 64 includes therein an illumination source 66 that comprises a plurality of LEDs. Twenty four (24) such LEDs are seen in FIG. 4 although more or less may be used. As seen in FIG. 4, each of the LED illumination sources 66 are arrayed along an arcuate interior surface of the housing 64. Each LED is butt-coupled to an optical fiber 68.

Each optical fiber 68 acts as a waveguide and the array of optical fibers 68 are tiled along an arc as illustrated in FIG. 4. In this scheme, since the diameter of each optical fiber core is ~0.1 mm, there is no need for a focusing lens or any other light coupling tool, which makes butt-coupling of each LED to its corresponding optical fiber end rather simple and mechanically robust. To increase the temporal coherence of the illumination source 66, the spectrum of the LEDs may be narrowed down to ~10 nm (centered at ~640 nm) using an optional interference based color filter 70. The opposing ends of each optical fiber 68 (the end not butt-coupled to the LED) is mounted on a common arc-shaped bridge 72. Thus, each optical fiber 68 is able to illuminate the sample from a different angle along the arc-shaped bridge 72. Unlike the prior embodiments, there is no need to move the illumination source to each different angle. Here, as explained below, individual LEDs are turned on which illuminate the sample at varying angles. The arc-shaped bridge, which may be made from plastic, has magnets 74 mounted at both ends. The magnets 74 may include rare earth magnets such as Neodymium magnets. The imager 62 includes coils 76 mounted adjacent to each magnet. The coils 76 are coupled to a DC current source that, when activated, generates an electromagnetic force that displaces the bridge 72 and simultaneously translates all of the ends of the fibers 68. In this regard, the arc-shaped bridge 72 with the magnets 74 and associated coils 76 act as an electromagnetic actuator. The coils 76 and/or magnets 74 are placed to generate an orthogonal displacement when its corresponding coil 76 is activated. Therefore, displacement of the ends of the fibers 68 occurs in both the x and y directions. The coils 76 are placed such that their cylindrical axes are aligned with the magnetization vector of the magnets.

A battery (not shown) could be used to power the imager 62. For example, standard alkaline batteries (with a capacity of e.g., 3000 mA h) could be used to actuate the fibers without the need for replacement for at least several days of continuous use of the tomographic microscope. Alternatively, the imager 62 could be powered by an external power source.

The imager 62 further includes a microcontroller 78 in the housing 64. The microcontroller 78 is used to control the firing of the LEDs that make up the illumination source 66. For instance, the microcontroller 78 may activate or trigger each individual LED at the appropriate time. As an example, the LEDs may be activated sequentially along the bridge 72. The microcontroller 78 may also be used to control the actuation of the coils 76.

Still referring to FIG. 4, the imager 62 includes a sample loader 80 that is moveable into and out of the housing 64. A sample 14 that contains one or more objects 12 (See FIG. 1B) is loaded onto a sample holder 18 and placed in the sample loader 80. The sample loader 80 is then pushed into the device, where the sample 14 is placed in the optical path of the illumination source 66. The imager 62 also includes an imager sensor 82. The image sensor 82 may include a CMOS or CCD as discussed in the context of the prior embodiments.

The system 60 further includes a computer 30 having at least one processor 32 therein that is used to execute software for the processing and analysis of images as in the prior embodiment. A monitor 34 and input device 36 may be connected to the computer 30 for displaying results and interfacing with the computer 30. The computer 30, monitor 34, and input device 36 operate in the same or similar manner as in the prior embodiments.

Experiment 1

First Embodiment

The embodiment illustrated in FIG. 1A was used for lens-free optical tomography, achieving <1 μm lateral resolution together with an axial resolution of ~2.5-3 μm over a large FOV of ~14 mm² as well as an extended DOF of ~4 mm, enabling an on-chip imaging volume of ~15 mm³. This lens-free optical tomography platform merges high resolution in 3D with a significantly large imaging volume, offering a 3D space-bandwidth product that is unmatched by existing optical computed tomography modalities.

Lens-free tomographic imaging is achieved by rotating a partially coherent light source with ~10 nm spectral bandwidth to illuminate the sample volume from multiple angles (spanning ±50° in air), where at each illumination angle several sub-pixel shifted inline projection holograms of the objects on the chip are recorded without using any lenses, lasers or other bulky optical components. Limited spatial and temporal coherence of the hologram recording geometry brings important advantages to the reconstructed images such as reduced speckle and multiple reflection interference noise terms. Furthermore, the unit fringe magnification in this geometry permits recording of inline holograms of the objects even at oblique illumination angles of e.g., >40° which would not be normally feasible with conventional coherent inline holographic imaging schemes that utilize fringe magnification.

In order to combat the limited angle artifacts in the tomograms, a dual-axis tomography scheme is employed by sequentially rotating the illumination source in two orthogonal directions as illustrated in FIG. 1A. To perform pixel super-resolution and hence achieve sub-micron lateral resolution for each projection image, multiple lens-free in-line holograms that are sub-pixel shifted (in the x-y plane) with respect to one another are acquired at every illumination angle (see inset of FIG. 1A). Once a set of high-resolution (SR) projection holograms (one for each illumination angle) are digitally synthesized using a pixel super-resolution algorithm, a hybrid filtered back-projection method is utilized to create the final tomograms of the objects. Therefore, the super-resolved projections are first digitally reconstructed, and then back-projected to obtain volumetric images of the scattering potential of the sample.

These results constitute the first time that (1) optical tomographic imaging has been extended to lens-free on-chip imaging; and (2) dual-axis tomography has been applied to optical part of the electro-magnetic spectrum; and (3) pixel super-resolution techniques have been applied for optical tomographic imaging. Without the use of any lenses or coherent sources such as lasers, the presented lens-free tomographic imaging scheme achieves a spatial resolution of <1 μm x<1 μm x~2.5-3 μm over a large imaging volume of ~15 mm³ using dual-axis tomography scheme. The imaging volume increases to ~30 mm³, at the cost of ~15% reduction in axial resolution, if only single-axis projection data is utilized. Offering good spatial resolution over a large imaging volume, lens-free optical tomography could in general be quite useful for high-throughput imaging applications in e.g., cell and developmental biology.

In the lens-free tomographic imaging setup used in this experiment, the light source, situated about $z_1$=70 mm away from the sensor (Aptina MT9P031STC, 5 Megapixels, 2.2 μm pixel size), provides partially coherent illumination to record inline holograms of the objects, whose distance to the sensor surface ranges between e.g., $z_2$=0.5-4 mm depending on the chamber height. For experimental flexibility, a monochromator was utilized to provide tunable broadband illumination with ~10 nm bandwidth centered around 500 nm. After being filtered through an aperture of diameter 0.05-0.1 mm and propagating a distance of $z_1$=70 mm, the illuminating beam acquires a spatial coherence diameter <0.5-1 mm which permits recording the inline holograms of individual objects. Multi-angle illumination is achieved by rotating the light source, using a motorized stage, along an arc whose origin is the center of the sensor array. Due to the large $z_1/z_2$ ratio, this alignment is not sensitive and robustness of the setup is maintained.

At every illumination angle, a series of sub-pixel shifted holograms are recorded for implementing pixel super-resolution (operation 1400 of FIG. 2), which is achieved by linearly translating the light source, using a motorized linear stage, to discrete positions in a 3×3 grid in the plane parallel to the sensor surface using step sizes of ~70 μm (nine images total). Note that because of the large $z_1/z_2$ ratio, such large shifts at the source plane correspond to sub-pixel shifts at the hologram plane. The exact values of these sub-pixel shifts are not critical, and in fact their values are digitally inferred from the amount of lateral shifts that the raw holograms experience as a function of the illumination angle.

Because most digital sensor arrays are designed to operate in lens-based imaging systems where the angle of incident rays measured from the sensor surface normal does not exceed 20°-30°, the waves incident with large k-vectors are sampled with increased artifacts and reduced SNR. Therefore, even though the detection NA of the system can reach the refractive index of the medium owing to the short $z_2$, it has been observed that the reconstructed projection images for angles above ±50° exhibit artifacts and including these projections for tomographic reconstruction can deteriorate the final image quality rather than improving it. Consequently, projections are acquired only within a tilt range of ±50°, with 2° angular increments.

In order to reduce the artifacts of limited angle tomography, the dual-axis tomography scheme was used. Accordingly, after the completion of recording the projections along one axis, the sensor, with the sample mounted on it, is rotated 90° using a computer controlled rotating stage to record a second set of projections along the orthogonal direction. A custom developed LabView interface is used to automate the data acquisition process and a total of 918 wide FOV lens-free holograms are recorded. Acquiring a set of 459 projections along one axis takes ~5 min with a frame rate of ~4 fps, which can significantly be improved by using a faster frame rate sensor.

Figures 5A, 5B, 5C:
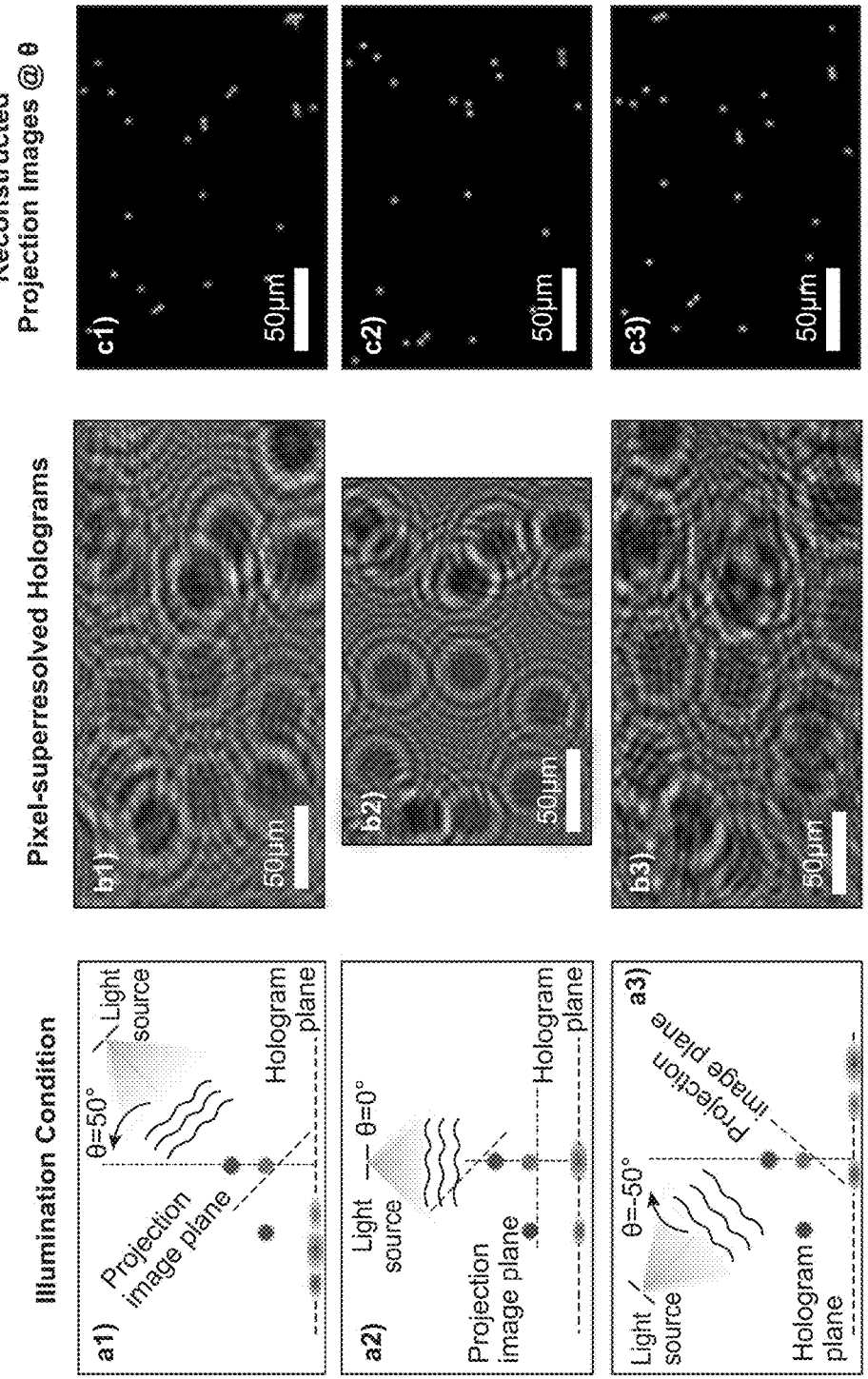
FIG. 5A schematically illustrates the holographic recording condition for three angles, +50°, 0°, and −50°, respectively. The light source, projection image plane, and hologram plane are shown for each condition.
FIG. 5B illustrates cropped images (b1, b2, b3) from corresponding super-resolved (higher resolution) holograms of 5 μm bead measured at the angled corresponding to three angles, +50°, 0°, and −50°, respectively.
FIG. 5C illustrates digitally reconstructed lens-free projection images (c1, c2, c3) using the corresponding holograms in FIG. 5B (images b1, b2, b3 respectively). Reconstruction was conducted at three angles, +50°, 0°, and −50°, respectively.

FIG. 5A schematically illustrates the holographic recording condition for three angles, +50°, 0°, and −50°, respectively. The light source, projection image plane, and hologram plane are shown for each condition. FIG. 5B illustrates cropped images (b1, b2, b3) from corresponding super-resolved (higher resolution) holograms of 5 µm bead measured at the angled corresponding to three angles, +50°, 0°, and −50°, respectively. The holograms of individual beads have an elliptical shape, as expected, since detection plane is not normal to beam propagation. FIG. 5C illustrates digitally reconstructed lens-free projection images using the corresponding holograms in FIG. 5B (images b1-b3). After perspective correction, the ellipticity is removed as revealed by the circular shape of the reconstructed beads. The reconstructed projection images are registered with respect to the bead at the center of the images, which is assumed to be the center-of-rotation.

Figure 6A:
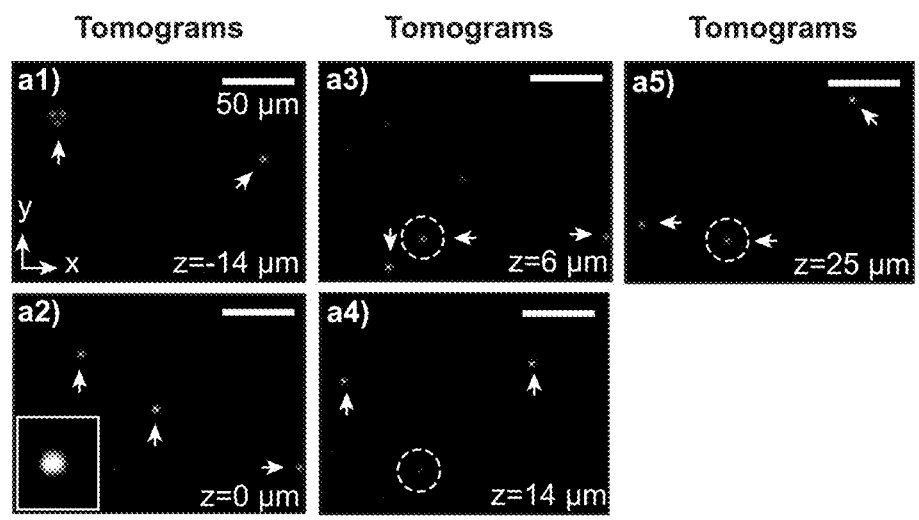
FIG. 6A illustrates dual-axis tomographic reconstruction results for 5 μm melamine beads (refractive index ~1.68, Corpuscular Inc.) distributed randomly in a ~50 μm thick chamber filled with an optical adhesive (refractive index ~1.52, Norland NOA65). Various planes within the chamber volume are illustrated (a1: 14 μm; a2: 0 μm; a3: 6 μm; a4: 14 μm; a5 25 μm).

To characterize the lens-free tomographic system, a series of experiments using microbeads of different dimensions was conducted. FIG. 6A illustrates the dual-axis tomographic reconstruction results for 5 µm melamine beads (refractive index ~1.68, Corpuscular Inc.) distributed randomly in a ~50 µm thick chamber filled with an optical adhesive (refractive index ~1.52, Norland NOA65). Computed tomograms are calculated at various planes ranging from −14 µm to 25 µm. In order to match the FOV of the objective lens (40×, 0.65-NA) that was utilized to obtain microscope comparison images (FIG. 6B), tomograms were computed, within <3 min using a Graphics Processing Unit (NVidia, Geforce GTX480), only for a small region of interest cropped from a much larger FOV of ~14 mm² image. The arrows in FIGS. 6A and 6B point out the beads, which are in-focus at a given layer. FIG. 6A (images a1-a5), together with their corresponding microscope comparisons provided in FIG. 6B (images b1-b5) reveal that the out-of-focus beads are successfully rejected in the tomograms, and only the in-focus beads appear in the reconstructed images. To further illustrate the tomographic imaging performance, FIG. 6C (images a6-a8) show a zoomed region of interest, highlighted by the dashed circles in FIG. 6A (images a3-a5), where two random beads axially overlap with a center-to-center separation of ~20 µm in z-direction. These images are displayed alongside corresponding microscope images (images b6 to b8). From these reconstruction results, it is clear that the overlapping beads are successfully resolved at their corresponding depths with minimal out-of-focus contamination from each other; and the intermediate slice shown in FIG. 6C (image a7) has negligible spurious details, indicating successful sectioning of this axially overlapping region. These results, as validated by their corresponding microscope images shown in FIG. 6B (images b1 to b5) and FIG. 6C (images b6 to b8), demonstrate a sectional imaging ability that is beyond the reach of regular inline holography schemes, regardless of their detection numerical aperture or the coherence properties of illumination source.

Figure 6B:
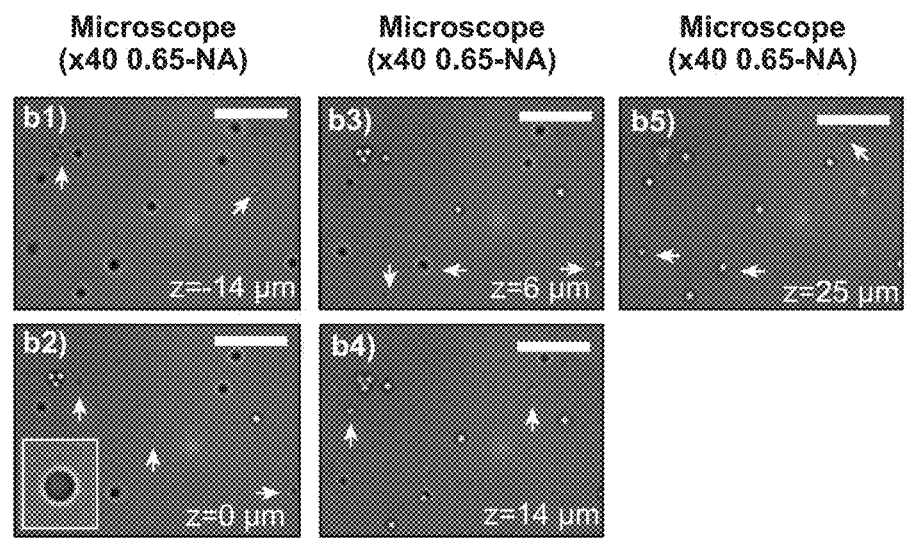
FIG. 6B illustrates microscope images (×40, 0.65NA) for the same planes in the corresponding tomograms in FIG. 6A.
Figure 6C:
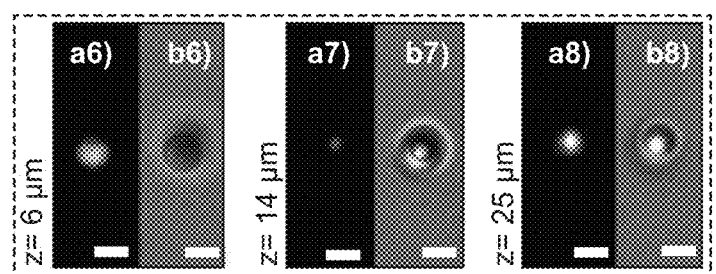
FIG. 6C illustrates zoomed regions of interest (images a6-a8), highlighted by the dashed circles in FIG. 6A (images a3-a5), where two random beads axially overlap with a center-to-center separation of ~20 μm in z-direction. These images are displayed alongside corresponding microscope images (images b6 to b8).

Although the results of FIGS. 6A-6C have been demonstrated over a relatively small FOV, tomograms of the entire imaging volume can be obtained by digitally combining several tomograms for different regions within the FOV that can all be calculated from the same raw holographic data set. It should be noted that the effective FOV reduces to ~14 mm² from 24 mm² (which is the active area of the CMOS sensor-chip) since the holograms of the objects close to edges of the sensor fall outside the active area at large angles of illumination.

Figure 7A:
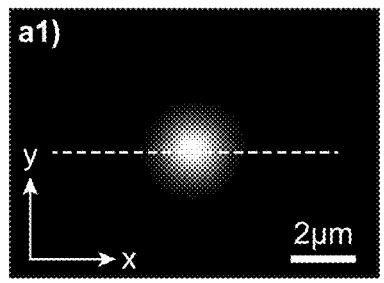
FIG. 7A illustrates the reconstructed cross section of a bead at z=−3 μm in the x-y plane (cutting through the center of the bead).
Figure 8A:
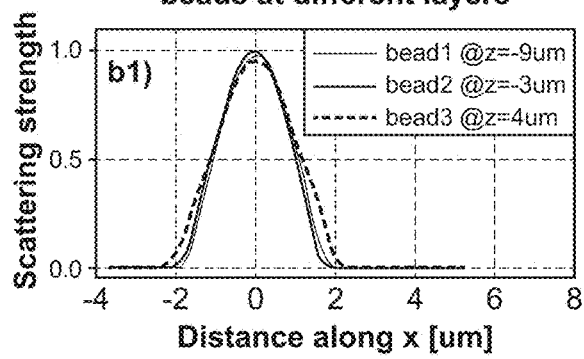
FIG. 8A shows the cross-sectional line-profiles along x-y cross-section for three separate beads located at different depths.
Figure 7B:
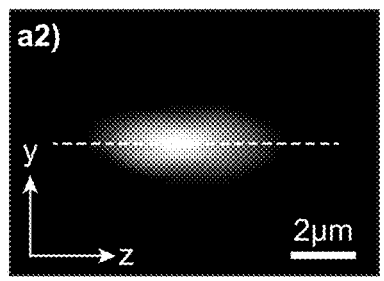
FIG. 7B illustrates the reconstructed cross section of a bead at z=−3 μm in the y-z plane (cutting through the center of the bead).
Figure 8B:
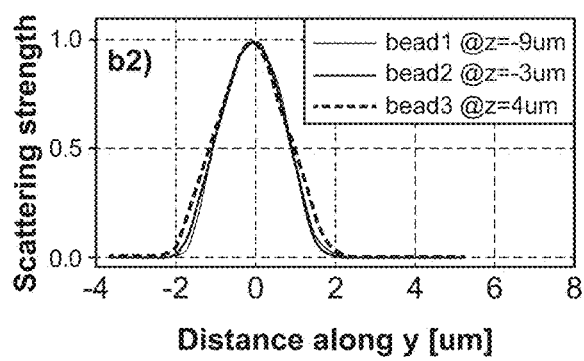
FIG. 8B shows the cross-sectional line-profiles along y-z cross-section for three separate beads located at different depths.
Figure 7C:
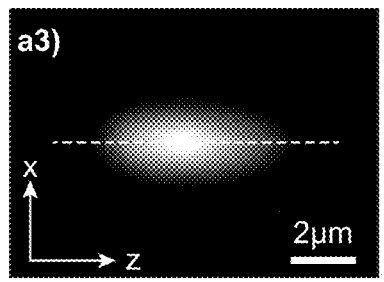
FIG. 7C illustrates the reconstructed cross section of a bead at z=−3 μm in the x-z plane (cutting through the center of the bead).
Figure 8C:
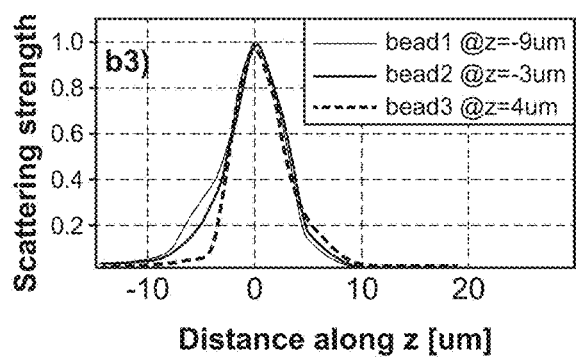
FIG. 8C shows the cross-sectional line-profiles along x-z cross-section for three separate beads located at different depths.

To further investigate the imaging properties of the tomographic microscope, 2 µm diameter beads distributed in an optical adhesive were imaged. FIGS. 7A-7C illustrate the reconstructed cross-sections in x-y, y-z and x-z planes, respectively, each cutting through the center of the bead. As revealed by the circular shape of the reconstructed bead in FIG. 7A, the dual-axis tomography scheme eliminates the elongation artifact in the x-y plane, which is normally observed in limited angle single-axis tomography. On the other hand, the reconstruction of the same bead still exhibits an axial elongation due to missing projections at angles larger than ±50° with respect to the normal of the sensor plane. FIGS. 8A-8C show cross-sectional line-profiles along x, y and z for three separate beads located at different depths. For the bead at z=−3 µm, the FWHM values for line profiles through the center are 2.3 µm, 2.2 µm and 5.5 µm, along x, y and z dimensions, respectively. Similar results have been obtained with other beads at depths z=−9 µm and z=4 µm, which shows that the same imaging performance is maintained at different depths of the visualized volume.

In addition to enabling 3D imaging of objects over a wide FOV, owing to its lens-free unit-magnification geometry, the platform also enjoys a significantly extended DOF compared to imaging systems where conventional microscope objectives are used. To demonstrate the large DOF, a multilayer chamber composed of 10 µm beads which has four layers stacked with ~1 mm separation. (i.e., having a total thickness of 3.3 mm) was imaged. The chamber is then elevated above the sensor active area, and the furthest layer is situated ~4 mm away from the sensor chip. With an illumination angle spanning ±50° in air, the entire tomographic data corresponding to a volume of 14 mm²×3.3 mm is acquired over ~10 minutes using dual-axis scanning. Once this raw data is acquired (which includes nine sub-pixel shifted holograms at each illumination angle), separate tomograms for each depth layer are computed. These tomograms are then digitally combined into a single volumetric image, which now has a DOF of ~4 mm Holographically recorded set of projections, one of which is illustrated in FIG. 9A, comprise the entire 3D volumetric information of the thick sample, and arrows of different sizes in FIG. 9A point to beads located at different layers within the multilayer chamber. FIGS. 9B-9E illustrate tomograms for different depths within the chamber (FIG. 9B: z=3.97 mm; FIG. 9C: z=1.740 mm; FIG. 9D: z=730 µm; FIG. 9E: z=742 µm).

Figures 10A, 10B, 10C:
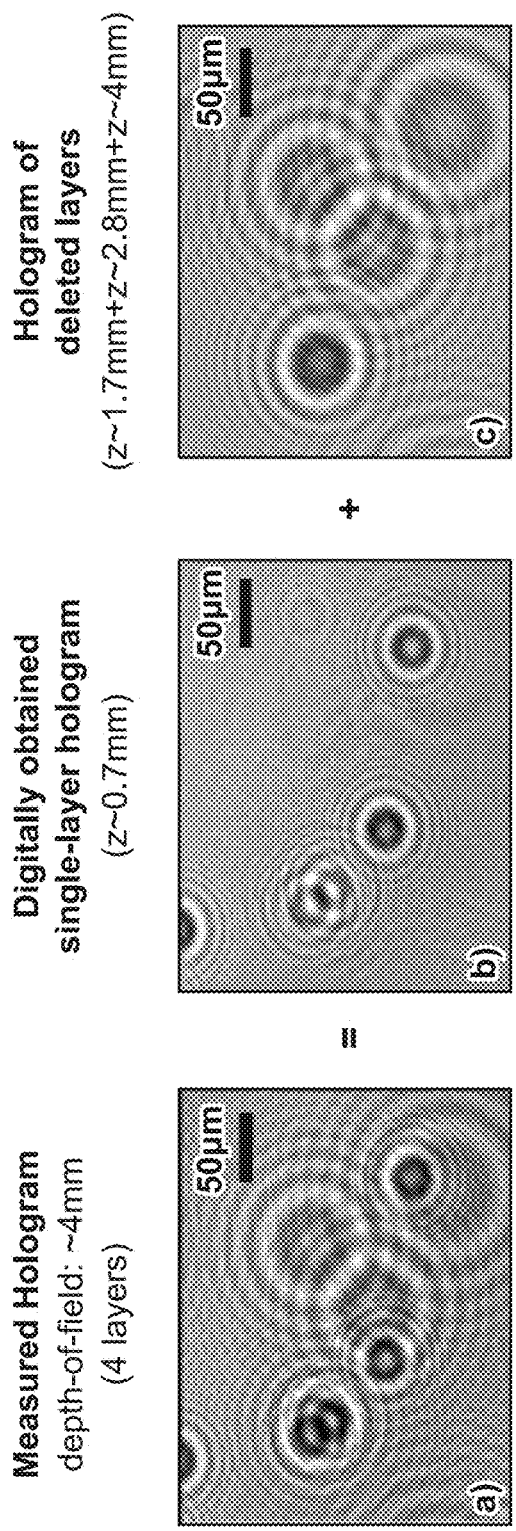
FIG. 10A illustrates the measured hologram of 10 μm beads distributed in a four layer chamber with total thickness of ~3.3 mm.
FIG. 10B illustrates the hologram of beads only in a given layer (layer 1 at z~0.7 mm) which has been digitally extracted, by reconstructing the measured hologram at the undesired depths, and removing their contribution from the total hologram field.
FIG. 10C illustrates the difference hologram, obtained by subtracting the digitally obtained single-layer hologram (FIG. 10B) from the measured multi-layer hologram (FIG. 10A).

One important challenge for tomographic reconstruction of such a large DOF is actually the implementation of pixel super-resolution at each illumination angle. Since the raw holograms of particles/objects that are located at considerably separated depths will create different shifts, if their holograms overlap at the detector plane, blind realization of pixel super-resolution will create errors for at least some of the overlapping particle holograms. To mitigate this challenge, the raw holograms of different layers were filtered from each other such that pixel super-resolution can be separately applied to lens-free holograms of different depth layers. Computing the super-resolved holographic projections for axially overlapping objects in thick samples requires additional digital processing due to the fact that the holograms of objects with an axial separation >200-300 μm shift significantly different amounts over the sensor-chip. As a result, the raw holograms obtained by shifting the light source are essentially different two-dimensional functions rather than translated versions of the same 2D raw hologram, which is a requirement to be met for the pixel super-resolution technique. Consequently, a single super-resolved projection hologram at a given illumination angle cannot be calculated for the entire sample depth. Instead, separate super-resolved holograms are calculated for each depth layer. To achieve this, the measured holographic projections such as the measured hologram of FIG. 10A are digitally reconstructed at each depth that is to be deleted, and the reconstructed objects are removed from the hologram field by multiplication with a binary mask which is zero inside the support of the objects and unity outside. Successively doing this operation for all the layers to be deleted within a thick volume, the digital hologram for only the layer of interest is obtained as seen in FIG. 10B. Because the masking operation is applied to undesired layers only, no artifact is introduced to the hologram for the layer of interest, as illustrated by FIG. 10C, which shows the difference between the original hologram and the digitally derived hologram for the layer of interest. Once the shifted holograms for a short depth range (<200-300 μm) are digitally obtained, a super-resolved hologram can be calculated specifically for the depth layer of interest as discussed in the earlier section.

Figure 11A:
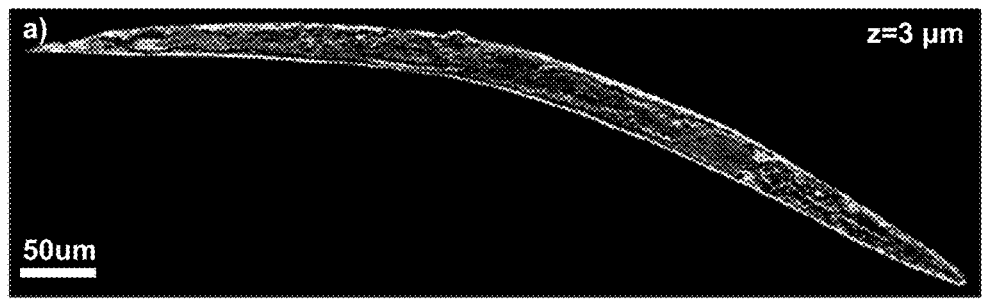
FIG. 11A illustrates a tomogram of *C. Elegans* corresponding to the z=3 μm plane.
Figure 11B:
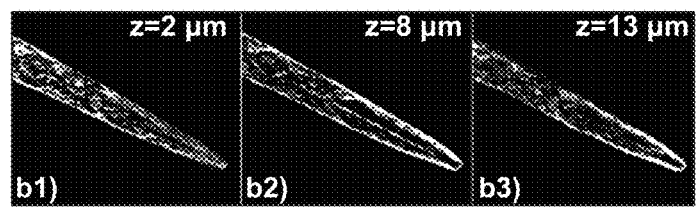
FIG. 11B illustrates tomograms of *C. Elegans* corresponding to the z=2 μm plane (b1); z=8 μm plane (b2); z=13 μm plane (b3).
Figure 11C:
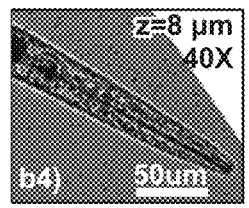
FIG. 11C illustrates a microscope image (×40, 0.65NA for comparison).
Figure 11D:
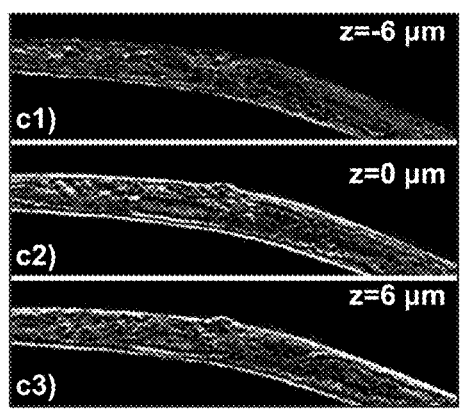
FIG. 11D illustrates tomograms of the middle part of *C. Elegans* corresponding to the z=−6 μm plane (c1); z=0 μm plane (c2); z=+6 μm plane (c3).
Figure 11E:
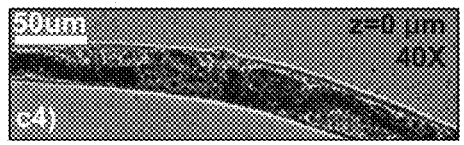
FIG. 11E illustrates a microscope image (×40, 0.65NA for comparison) of the middle part of the worm for comparison.

In order to demonstrate the performance of the lens-free tomographic microscope for applications in life sciences, a wild-type *C. Elegans* worm was imaged in L4 stage (~650 μm in length) in deionized water. The worm was temporarily immobilized with 4 mM levamisole (Sigma Aldrich L9756) solution to avoid undesired motion during the imaging process. Because the worm was aligned parallel to y-axis during data acquisition, only the projections obtained by tilts along the x-axis were utilized to compute the tomograms of the worm, which took ~4 min using a single GPU. FIG. 11A shows a slice through the whole worm corresponding to the z=3 μm plane. The worm was observed to be slightly tilted out-of-plane with respect to the sensor surface, with its anterior elevated by ~8 μm, as a result of which a single slice through the entire worm does not reveal the details across the animal with equal sharpness. FIG. 11B (images b1-b3) show three reconstructed depth sections through the anterior region of the worm at the z=2 μm, z=8 μm and z=13 μm planes, respectively. Image b4 of FIG. 11C illustrates a microscope image (×40, 0.65 NA) for comparison. As shown in these figures, the pharyngeal tube of the worm, which is a long cylindrical structure with <5 μm outer diameter, is clearly visible at the z=8 μm plane (imaged b2) while it quickly disappears at depths away from the center of the pharynx. FIG. 11D (images c1-c3) also show the tomograms at different depths through the center and anterior regions of the same worm. FIG. 11E (Image c-4) illustrates a microscope image for comparison. In all these results, the appearance of distinct details at different sections can clearly be observed, demonstrating a significantly improved sectioning ability that is otherwise unattainable with regular in-line holographic reconstructions, regardless of their detection numerical apertures or coherence properties. Together with its large imaging volume, these results reveal the potential of the lens-free tomography platform for on-chip imaging and screening of optically accessible model organisms such as *C. Elegans* and zebrafish, where high-throughput imaging is of utmost importance.

The lens-free tomographic imaging system provides a unique microscopy modality that can probe a wide FOV of ~14 mm$^2$ and a long DOF of ~4 mm at a lateral resolution of <1 μm and an axial resolution of ~2.5-3 μm. These results suggest a resolving power that is comparable to a standard 20× objective lens (NA~0.4, FOV <1 mm$^2$) but over >10$^4$ times larger imaging volume. This makes the platform especially suitable for high-throughput imaging and screening applications such as 3D model animal imaging. Also note that the imaging volume can be increased to ~30 mm$^3$ by utilizing projections acquired with a single-axis data set, at the cost of a lower axial resolution of ~3-3.5 μm.

There are several unique aspects of the lens-free incoherent holography scheme that enable achieving on-chip tomographic imaging over such a wide FOV and an extended DOF. For instance, choosing a large $z_1/z_2$ ratio of ~20-100 allows holographic imaging with unit magnification, which brings the large FOV to this imaging modality. The limited hologram resolution dictated by this unit-magnification and the pixel-size at the sensor-chip is balanced by a pixel super-resolution approach, which increases the lateral numerical aperture up to 0.4-0.5 without a trade off in imaging FOV. The same large $z_1/z_2$ ratio also permits the use of unusually large illumination apertures (e.g., >50 μm), which significantly simplifies the illumination end without the need for any light-coupling optics, a sensitive alignment or a trade-off in achievable resolution. As a result, projections are easily acquired by tilting the light source rather than having to rotate the object which would unnecessarily complicate the setup, and perturb the sample. Moreover, the simplicity of the optics and the alignment-free structure of the lens-free setup also permit straightforward implementation of dual-axis tomography, since either the tilt-axis of the light source or the sensor (with the sample mounted on it) can be rotated 90° to acquire projections along two orthogonal directions.

Another unique aspect of the lens-free tomography scheme is the use of partially coherent light, both temporally and spatially. The spectral width of the illumination is ~10 nm with a center wavelength of ~500 nm, which limits the coherence length to be <10 μm. This relatively short coherence length does not impose any limitations for the technique and in fact, it significantly reduces two major sources of noise, i.e., the speckle and multiple-reflection interference noise terms. The latter one would especially have been a nuisance under laser illumination at oblique angles. In addition, such a limited coherence length also partially eliminates the cross-talk of different depths with each other. Such cross-interference terms are undesired and in fact are entirely ignored in any holographic reconstruction scheme. The same cross-interference also occurs within a given depth layer. In other words, scattering centers within the sample volume actually interfere with each other at the detector plane, which once again is a source of artifact as far as holographic reconstruction (e.g., twin-image elimination)

is concerned. The limited spatial coherence also helps us to mitigate this issue by choosing a spatial coherence diameter (e.g., <0.5-1 mm) that is sufficiently large to record individual holograms of the objects, and yet that is significantly smaller than the entire imaging FOV. This spatial coherence diameter is rather straightforward to engineer in this geometry by changing the illumination aperture (e.g., 0.05-0.1 mm) as well as by changing the distance between the source aperture and the sample volume.

Experiment 2

Second Embodiment

In this experiment, the embodiment of FIG. 3 was tested as an optofluidic tomographic microscope, which can perform 3D imaging of specimen flowing within a microfluidic channel. In this optofluidic lens-free imaging modality, using a spatially incoherent light source (600 nm center wavelength with ~10 nm spectral bandwidth, filtered by an aperture of diameter ~0.05-0.1 mm) placed ~50 mm away from the sensor, digital in-line holograms of the sample are recorded by an optoelectronic sensor array (Aptina MT9P031STC, 5 Megapixels, 2.2 µm pixel size). While the holograms are being acquired, the objects are driven by electro-kinetic flow along a micro-channel which is placed directly on the sensor with a slight tilt in the x-y plane as seen in FIG. 3. The exact value of this tilt angle is not critical and need not be known a priori; it simply ensures that the flow of the object along the micro-channel generates a shift component in both x and y, enabling digital synthesis of higher resolution holograms through pixel super-resolution. Owing to its unique hologram recording geometry with unit fringe magnification, the holographic optofluidic microscopy platform permits imaging of the flowing objects using multiple illumination angles as shown in FIG. 3, which is the key to achieve optical computed tomography.

Multi-angle illumination for tomographic imaging would not be feasible with conventional optofluidic microscopy architectures because at higher illumination angles the projection images of different cross-sections of the same object would start to lose resolution due to increased distance and diffraction between the object and the aperture/sensor planes. In this optofluidic tomography platform, at each illumination angle (spanning e.g., $\theta=-50°:+50°$ several projection holograms (i.e. 15 frames) are recorded while the sample flows rigidly above the sensor array. These lower-resolution (LR) lens-free holograms are then digitally synthesized into a single super-resolved (SR) hologram by using pixel super-resolution techniques to achieve a lateral resolution of <1 µm for each projection hologram corresponding to a given illumination direction. These SR projection holograms are digitally reconstructed to obtain complex projection images of the same object, which can then be back-projected using a filtered back-projection algorithm to compute tomograms of the objects.

Figures 11F, 11G:
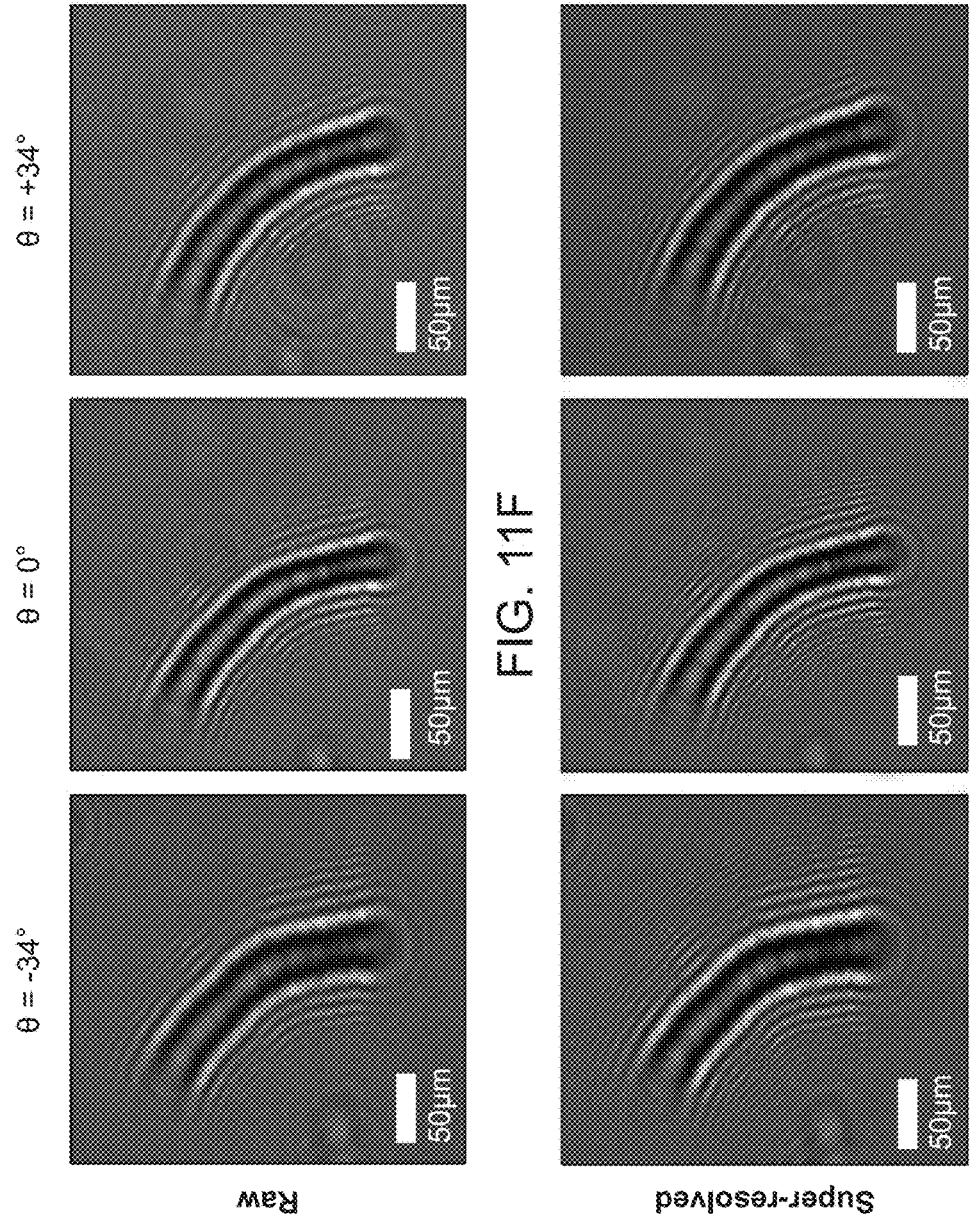
FIG. 11F shows lensfree raw holograms of *C. Elegans* sample at three different illumination angles (θ=0°, 34°, and -34°).
FIG. 11G show three reconstructed (super-resolved holograms) at the three angles of FIG. 11F.
Figures 12A, 12B, 12C, 12D:
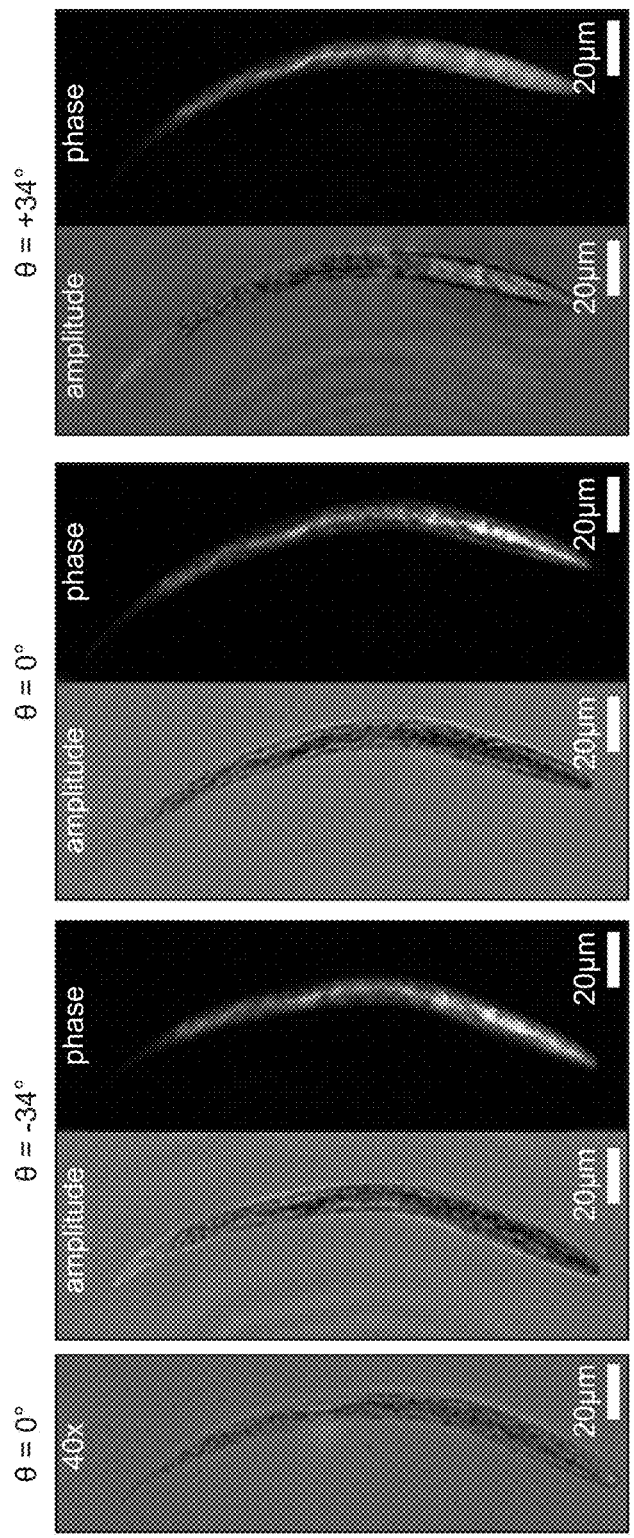
FIG. 12A illustrates a 40× objective-lens microscope image corresponding to the vertical cross-section of the worm.
FIG. 12B illustrates the amplitude and phase reconstruction images of the worm taken at an angle of −34°.
FIG. 12C illustrates the amplitude and phase reconstruction images of the worm taken at an angle of 0°.
FIG. 12D illustrates the amplitude and phase reconstruction images of the worm taken at an angle of +34°.

An experiment was conducted where a wild-type *C. elegans* worm was sequentially imaged during its flow within a microfluidic channel at various illumination angles spanning $\theta=-50°:+50°$ in discrete increments of 2°. In these experiments, the design of the CMOS sensor-chip utilized for experiments ultimately limits the maximum useful angle of illumination. Most digital sensors are designed to work in lens-based imaging systems and therefore holograms recorded at illumination angles larger than ±50° exhibit artifacts. For this reason, we have limited the angular range to ±50°. For each illumination angle, ~15 holographic frames were captured of the flowing object (in <3 seconds), resulting in a total imaging time of ~2.5 minutes per tomogram under the electro-kinetic flow condition. These illumination angles are automatically created by a computer-controlled rotation stage holding the light source, and they define rotation of the source within the x-z plane with respect to the detector array, which is located at the x-y plane. Some exemplary LR holograms recorded with this set-up are illustrated in FIG. 11F. As expected, for the tilted illuminations ($\theta=\pm34°$) the extent of the holograms along x are wider compared to $\theta=0°$ case. By using the sub-pixel shifts of the worm during its flow within the micro-channel, super-resolved holograms are synthesized of the sample at each illumination angle as also illustrated in FIG. 11G. Namely, multiple, sub-pixel images are used to create a single, higher resolution image as seen in operation 1400 of FIG. 2. These SR holograms exhibit finer fringes which are under-sampled in the raw holograms.

To obtain complex projection images of the sample through digital holographic reconstruction, the synthesized SR holograms are digitally multiplied with a tilted reference wave. The tilt angle of this reconstruction wave is not equal to the tilt of the light source, because of the refraction of light in the microfluidic chamber. Instead, the digital reconstruction angle ($\theta$) for projection holograms are determined by calculating the inverse tangent of the ratio $\Delta d/z_2$, where $\Delta d$ denotes the lateral shifts of the holograms of objects with respect to their positions in the vertical projection image, and $z_2$ can be either experimentally known, or determined by the digital reconstruction distance of the vertical projection hologram. It should be noted that despite the use of tilted illumination angles, the recorded holograms are still in-line holograms since the reference wave and the object wave propagate co-axially. As a result, an iterative phase recovery algorithm based on object-support constraint is utilized to reconstruct the complex field transmitted through the object. Throughout these iterations, the optical field is propagated back and forth between the parallel hologram and object planes. Once the iterations converge, the projection of the complex field in the plane normal to the illumination angle is obtained by interpolating the recovered field on a grid whose dimension along the tilt direction is rescaled by $\cos(\theta)$. Exemplary reconstructions are shown in FIGS. 12A-12D for $\theta=\pm34°$ and 0°, which demonstrates the multi-angle super-resolved imaging performance of the holographic optofluidic microscopy platform. The entire process of calculating a SR hologram and iteratively reconstructing the image within ~15 iterations takes less than 0.25 seconds using a parallel CUDA-based implementation on a Graphics Processing Unit (GPU-NVidia Geforce GTX 480).

For weakly scattering objects, the complex field obtained through digital holographic reconstruction (as shown in FIGS. 12A-12D) represents the projection of the object's complex transmission function (phase, absorption or scattering potential) along the direction of illumination. Therefore, the 3D transmission function of the object can be computed in the form of a tomogram using a filtered back-projection algorithm where all the complex projection images (i.e., 51 super-resolved images for $\theta=-50°:2°:50°$) are used as input. FIGS. 13A-13E illustrate a lens-free optofluidic tomogram of a *C. elegans* sample where several depth sections of the worm are provided. FIG. 13F illustrates a 10× microscope image. Such a tomographic imaging scheme especially mitigates the well-known depth-of-focus problem inherent in holographic reconstruction modalities, and allows optofluidic tomographic imaging with significantly improved axial resolution. This entire tomographic reconstruction process (including the synthesis of the SR holograms and the filtered back-projection) takes less than 3.5 minutes using a single GPU, which can be significantly improved by using several GPUs in parallel. Based on these tomographic reconstruction results, the Full-Width-Half-Maximum (FWHM) of the axial line-profile of the amplitude of the worm's transmission was measured as ~30 µm, which agrees well with the typical thickness of a C. elegans sample. Without computing tomograms, the same axial FWHM using a single super-resolved vertical lens-free hologram ($\theta=0°$) would have been ~1 mm, which clearly demonstrates the depth of focus improvement using multiple projections. The long depth-of-focus inherent to the lens-free holograms indeed helps to satisfy the projection approximation for an extended depth-of-field, permitting tomographic imaging of weakly scattering samples such as C. Elegans.

Due to the limited angular range of holograms that can be recorded, there is a missing region in the Fourier space of the object, commonly known as the "missing wedge". The most significant effect of the missing wedge is the elongation of the PSF in the axial direction, which limits the axial resolution to a value larger than the lateral, which is estimated to be ~3 µm in this case. Reduction of such artifacts can be achieved by implementing iterative constraint algorithms either based on the 3D support of the object or by utilizing a priori information about the transmission function of the object, which enables iteratively filling the missing region in the 3D Fourier space of the object function.

Experiment 3

Third Embodiment

Embodiment three relates to a field-portable lens-free tomographic microscope that can achieve depth sectioning of objects on a chip. This compact lens-free optical tomographic microscope, weighing only ~110 grams, is based on partially-coherent digital in-line holography and can achieve an axial resolution of <7 µm over a large FOV of ~20 mm$^2$ and a depth-of-field (DOF) of ~1 mm, probing a large sample volume of ~20 mm$^3$ on a chip. By extending the DOF to ~4 mm, the imaging volume can also be increased to ~80 mm$^3$ at the cost of reduced spatial resolution.

In this field-portable lens-free tomographic platform, the major factors that enable a significantly enhanced 3D spatial resolution are: (i) to record multiple digital in-line holograms of objects with varying illumination angles for tomographic imaging; and (ii) to implement pixel super-resolution to significantly increase the lateral resolution of lens-free holograms at each viewing angle. For implementation of this tomographic on-chip microscope, twenty four (24) light-emitting diodes (LEDs—each with a cost of <0.3USD) that are individually butt-coupled to an array of fiber-optic waveguides tiled along an arc as illustrated in FIG. 4. Each fiber has a core diameter of ~0.1 mm and a length of ~14 mm. The fibers are mounted along an arc such that they illuminate the sample from different angles, within a range of ±50° with ~4.1° increments. In this scheme, since the diameter of each fiber core is ~0.1 mm, there is no need for a focusing lens or any other light coupling tool, which makes butt-coupling of each LED to its corresponding fiber-end rather simple and mechanically robust. To increase the temporal coherence of the illumination source, the spectrum of the LEDs was narrowed down to ~10 nm (cent red at ~640 nm) using six pieces of interference based color filters (<50USD total cost, Edmund Optics) mounted on a piecewise arc that matches the geometry of the fiber optic array (~10 mm×5 mm) This ensures near-normal incidence of light on these color filters. After this spectral filtering, the coherence length of the illuminating beam increases to ~30 µm, which permits obtaining holograms with a numerical aperture (NA) of ~0.3-0.4 up to an object height of ~1 mm from the sensor-chip surface.

In order to record lens-free projection holograms from multiple angles, the LEDs are sequentially and automatically turned on/off by a low-cost micro-controller (Atmel ATmega8515, ~3 USD/per piece). A digital sensor array (Aptina MT9P031STC, 5 Megapixels, 2.2 µm pixel size), which is placed $z_1=~60$ mm away from the fiber-ends records the lens-free projection holograms of the objects that are loaded (with $z_2<5$ mm distance to the active area of the sensor-chip) through a sample tray inserted from one side of the lens-free microscope (see FIG. 4). At each illumination angle, a series of sub-pixel shifted holograms are recorded for implementing digital pixel super-resolution. For this purpose, all the fibers are mounted on a common arc-shaped bridge, which has Neodymium magnets at both ends. By driving the coils mounted across these magnets with a DC current, electromagnetic force is generated that actuates the plastic bridge and simultaneously translates all the fiber-ends. These fibers are shifted to 10-15 different locations within a ~500 µm×~500 µm grid, and for each position a new set of ~20-24 holographic projections are acquired. Note that such large shifts at the source plane correspond to much smaller shifts at the hologram plane because of the large $z_1/z_2$ ratio. More importantly, these shifts do not need to be accurate or repeatable since almost random shifts are equally valuable to achieve pixel super-resolution. Further, there is no need for prior knowledge of these shifts since this information can be accurately obtained by processing the sequence of the acquired lens-free holograms. Using LabView (National Instruments) based auto-exposure software, a set of 24 images can be acquired in ~6 sec at 4 frames/sec, which can be significantly sped up using a sensor with higher frame rate of e.g., >15-20 fps.

Despite the fact that the large $z_1/z_2$ ratio in the hologram recording geometry permits recording of holograms at angles close to ±90°, the design of digital sensor array itself restricts the actual range of illumination angles that can be used in the tomographic microscope. Most digital sensor arrays are designed for imaging systems that use lenses as imaging elements, as a result of which the angle of incident rays measured from the sensor surface normal is typically less than 20°-30°. Therefore, the sensitivity of these optoelectronic sensors, by design, rapidly drops for incidence angles that are larger than 50° and aberrations become significant. Therefore, even though the hologram recording geometry permits the use of higher angles (e.g. 70°-80°), we limit the angular range of illumination to ±50° for this particular tomographic microscopy set-up.

As described earlier, the optical fibers that are used for multi-angle illumination are connected to a common arc-shaped lightweight bridge (~1.7 grams), which moves together with all the fibers when actuated by electromagnetic forces. The other ends of these fiber-optic cables are mechanically fixed and are butt-coupled to individually addressed LEDs. Therefore, the entire structure can be modeled as a spring-mass system, where all the fibers collectively act as a spring, and the bridge piece is the mass load.

There are several critical specifications that need to be taken into account for the design of this structure: (1) to keep the form factor of the instrument small, the overall architecture of the actuator should be as compact as possible; (2) the structure should be stiff enough to stay rigid by itself such that small external perturbations do not randomly move the fiber tips during image acquisition, which would otherwise cause blurring of the recorded holograms; (3) the natural mechanical resonant frequency of the lowest vibrational mode of the structure should be as high as possible such that the structure does not move due to coupling of external vibrations, which also helps the fiber ends to reach the steady-state displacement rapidly without swinging for a long duration; and (4) sufficient actuation should be achieved with reasonable current and voltage values that can be supplied using standard batteries for field use. While (1), (2) and (3) can be achieved by keeping the fibers short, which makes the structure compact and stiff (also increasing the resonant frequencies), this would unfortunately demand a significant increase in the required electromagnetic force, and thereby would result in high electrical power consumption.

To better analyze this mechanical system, we assume a simple model where each fiber-optic waveguide acts as a cantilever beam with a cylindrical cross-section such that the stiffness (k) of the structure can be written as:

$$k = \frac{3E\pi r^4}{4L^3} \quad (1)$$

Where E is the Young's modulus of the silica fiber (E=72 GPa), r is the radius of the fiber (r=~62.5 μm) and L is the length of the fibers. In this lens-free tomographic microscope design, a fiber length of L=14 mm was chosen which is the distance between the plastic bridge to the fixed-end of the fibers. Assuming that these fibers act as parallel springs forming a lumped system of N=24 fibers, one can calculate the mechanical frequency of the structure as:

$$f_0 = \frac{1}{2\pi}\sqrt{\frac{N \cdot k}{m}} \quad (2)$$

Equation (2) yields an expected value of $f_0$~24 Hz when a measured mass of m=1.7 grams is used for the plastic bridge and the two magnets. According to this calculation, the time to reach the steady-steady displacement for the fibers once a force is applied can be estimated as ~300 ms assuming a quality factor of e.g., ~45. The actual settlement time of the fibers is short, supporting these calculations. Furthermore, during the experiments no undesired swinging of the fiber-array was observed due to external perturbations, and the entire structure is quite robust and sturdy making it suitable for field use.

To achieve electromagnetic actuation of the illumination fibers, two Neodymium magnets were mounted at each end of the plastic bridge. One of these magnets is aligned such that, when a DC current is applied to the coil mounted across it with ~1-2 mm distance, the electromagnetic force moves the fibers along the direction of the arc. The other magnet is placed to generate an orthogonal displacement when its corresponding coil is operated. Therefore, displacements of the fiber-ends in both x and y directions can be achieved to generate super-resolved projection holograms of the samples. These coils are placed such that their cylindrical axes are aligned with the magnetization vector of the magnets. In this configuration, the force generated on the magnets ($F_{mag}$) can be calculated as:

$$F_{mag} = S \cdot M \cdot (H_{z1} - H_{z2}) = S \cdot M \cdot \Delta H_z \quad (3)$$

where S is the cylindrical cross-sectional area (in units of $m^2$) of the magnet, M is the magnetization (in Tesla), $H_{z1}$ and $H_{z2}$ (in A/m) are the axial components of the magnetic field intensity at the top and bottom of the magnet, respectively. As Equation (3) suggests, the generated force is directly proportional to the magnetic field difference, $\Delta H_z$, across the two ends of the magnet, and it can be used to pull or push the magnet along the cylindrical axis depending on the polarity of the applied current.

As illustrated in FIG. 4, the sample to be imaged can be placed on a standard coverglass, which is positioned on the top of the sensor array using a sample tray inserted from one side of the portable tomographic microscope. Since the sample is much closer to the active area of the sensor-array (<4-5 mm) compared to its distance to the light source (~60 mm), lens-free holograms of objects can be recorded over a wide FOV of e.g., ~24 $mm^2$, which is >20 fold larger than the FOV of e.g., a typical 10× objective-lens. The low-cost micro-controller is then used to automatically and sequentially switch on the LEDs (one at a time) to record lens-free projection holograms of the sample within an angular range of ±50°.

In order to perform pixel super-resolution (SR) for enhancing the spatial resolution at each illumination angle, the fiber-optic waveguide ends are mechanically displaced by small amounts (<500 μm) through electromagnetic actuation. In this scheme, the fibers are connected to a common bridge (radius: 3.1 mm, length:6.2 mm) with low-cost Neodymium magnets attached on both ends. Compact circular electro-coils (radius:5 mm, height:5 mm) are mounted inside the plastic housing, which are used to electromagnetically actuate the magnets, resulting in simultaneous shift of all the fibers along both the x and y directions.

The exact amounts of displacement for these fiber-ends do not need to be known beforehand or even be repeatable or accurately controlled. As a matter of fact, the individual displacement of each fiber-end can be digitally calculated using the acquired lens-free hologram sequence. Once the fibers are shifted to a new position by driving the coils with a DC current, a new set of lens-free projection holograms are recorded, each of which is slightly shifted in 2D with respect to the sensor array. A maximum current of 80 mA is required for the largest fiber displacement (i.e., <500 μm), with ~4 volts of potential difference applied across the electro-coil (50Ω). Standard alkaline batteries (with a capacity of e.g., 3000 mAh) could be used to actuate the fibers without the need for replacement for at least several days of continuous use of the tomographic microscope.

With the above described set-up, 10-15 projection holograms are recorded at each illumination angle to digitally synthesize one SR hologram for a given illumination angle. FIG. 14A illustrates the hologram recording geometry for three different angles (−44°, 0°, and +44)°. FIG. 14B illustrates the corresponding pixel super-resolved (SR) projection holograms obtain at each corresponding angle of FIG. 14A. These lens-free SR holograms are digitally reconstructed to obtain projection images of the samples which is seen in FIG. 14C, which can then be merged together using a filtered back-projection algorithm to compute tomograms of the objects located on the sensor-chip.

The shifted holograms recorded at each illumination angle are digitally processed to synthesize projection holograms with higher spatial resolution. This is illustrated as operation 1400 in FIG. 2. These digitally synthesized super-resolved holograms are then rapidly reconstructed to obtain lens-free projection images of the objects. Despite the use of oblique illumination angles, the object wave and the unperturbed reference wave propagate co-axially, and each lens-free hologram is still an in-line hologram. In order to eliminate the twin-image artifacts and recover the phase of the recorded optical field intensity, an iterative phase retrieval algorithm is used where the hologram field is propagated back-and-forth between the detector and object planes using the object support as a constraint during these iterations. Similar to conventional holographic reconstruction, the recorded hologram should be digitally multiplied by a reconstruction wave that is the digital replica of the reference wave utilized for recording the holograms. Therefore, prior to the iterative phase recovery steps, the holograms are first multiplied with a plane wave that is tilted by an angle of $\theta_{rec}$. It is also important to note that the tilt angle of this reconstruction wave, $\theta_{rec}$, is not equal to the physical tilt of the illumination fiber due to the refraction of light within the sample chamber. In fact, $\theta_{rec}$ is determined by calculating the inverse tangent of the ratio $\Delta d/z_2$, where $\Delta d$ denotes the lateral shift of the raw holograms with respect to their positions in the vertical projection hologram, and $z_2$ is either experimentally known, or is determined by the digital reconstruction distance of the vertical holographic images. Convergence is typically achieved in 10-20 iterations, after which the optical field in the object plane parallel to the detector is obtained. Nevertheless, this field needs to be rotated to obtain the projection image that is normal to the direction of illumination. To achieve that, the recovered field is interpolated on a new grid that is resealed by $\cos(\theta_{rec})$ along the direction of the illumination tilt, which effectively squeezes the recovered field, and provides the projection image for the corresponding angle.

Figure 14C:
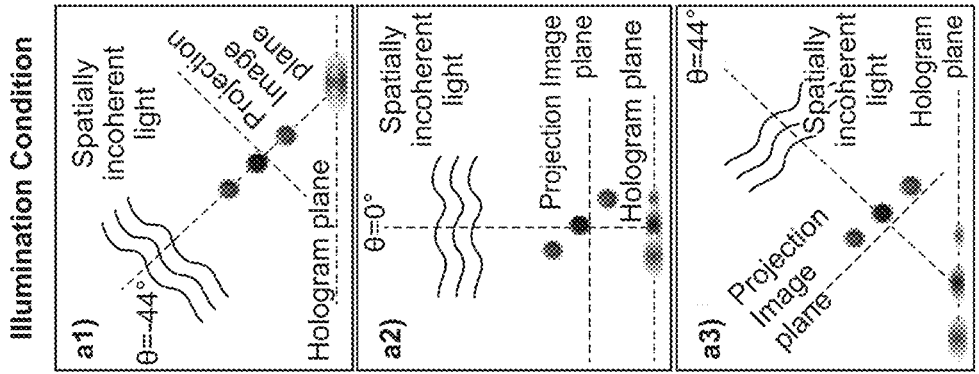
FIG. 14C illustrates digitally reconstructed lens-free projection images (c1, c2, c3) using the corresponding holograms in FIG. 14B (images b1, b2, b3 respectively). Reconstruction was conducted at three angles, −44°, 0°, and +44°, respectively.
Figure 14B:
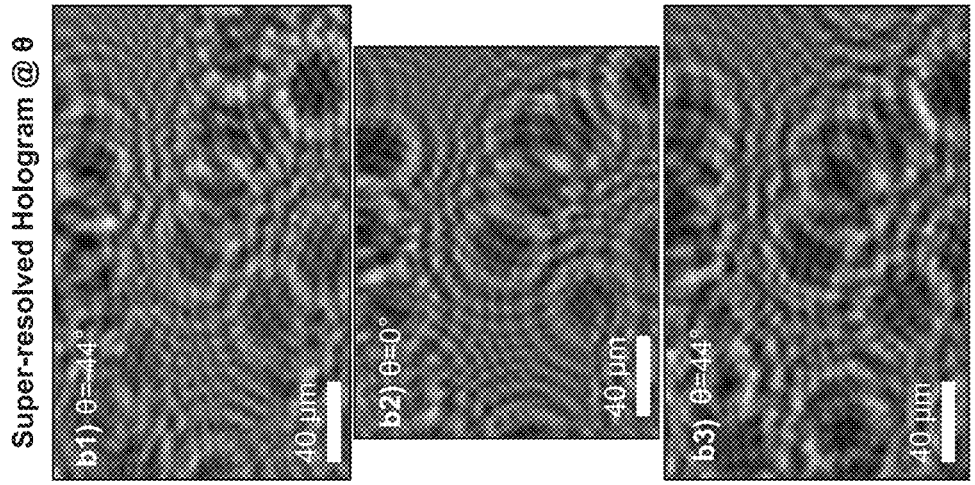
FIG. 14B illustrates cropped images (b1, b2, b3) from corresponding super-resolved (higher resolution) holograms of microbeads measured at the angled corresponding to three angles, −44°, 0°, and +44°, respectively.
Figure 14A:
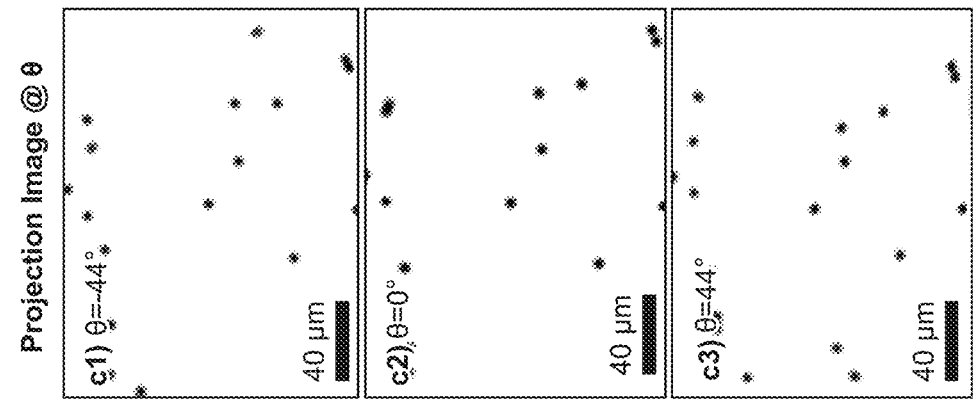
FIG. 14A schematically illustrates the holographic recording condition for three angles, −44°, 0°, and +44°, respectively. The light source, projection image plane, and hologram plane are shown for each condition.

Once the projection images at each illumination angle are calculated, they need to be registered with respect to a common center-of-rotation before computing the tomograms (see e.g., FIG. 14C (images c1-c3) where the three projection images are aligned with respect to the bead at the center). This is achieved by implementing an automated two-step cross-correlation algorithm. In the first step, the projection images for adjacent angles are aligned with respect to each other by cross-correlating the entire area of interest of these adjacent projections (e.g. 42° and 46°; 46° and 50°). Since the projection images for consecutive angles are very similar to each other, this operation provides an approximate initial alignment. However, this registration is not perfect due to slight changes of the scene as a function of viewing angle. In the second fine-alignment step, one of the projection images is selected as the global reference image, and all projection images are registered with respect to this reference image, but this time utilizing a smaller region of interest in the projections. This second step is especially required when aligning images of distributed small objects such as micro beads.

The filtered back-projection algorithm (described in more detail in the Radermacher M. publication incorporated herein by reference) is utilized to compute tomograms of the objects from their lens-free projection images. A fundamental requirement for the validity of this approach is that the projection images should represent a linear summation of a property of the object for which tomograms are being computed (e.g. phase, absorption, scattering strength, etc.). This is generally satisfied by weakly scattering objects in which case the majority of the incident photons experience at most a single scattering event over the volume of the object.

Assume that a weakly scattering object is represented by a complex scattering function $s(x_\theta,y_\theta,z_\theta)$, which satisfies $|s(x_\theta,y_\theta,z_\theta)| \ll 1$ where $(x_\theta,y_\theta,z_\theta)$ defines a coordinate system whose z-axis is aligned with the direction of illumination angle at a particular projection angle. In this case, the contribution of cross-interference terms to the hologram will be negligible in comparison to the actual holographic heterodyne terms. This assumption is further validated by the low spatial coherence (which minimizes cross-talk between objects with lateral separation larger than coherence diameter) and low temporal coherence (which minimizes the cross-talk between different layers with separation longer than coherence length) of the system, acting as a 3D coherence filter. As a result, for each projection image within a single tomogram volume (spanning e.g., $\Delta z \sim \pm 25$ μm), the holographically reconstructed image contrast will yield the linear summation of the scattering strength function given by: $\int s(x_\theta,y_\theta,z_\theta) \cdot dz_\theta$. This conclusion is further justified by the fact that, regardless of their detection numerical apertures, digital in-line holography schemes in general have a very long depth of focus as a result of which the scattering coefficients along a given $z_\theta$ direction can be approximated to add up linearly after appropriate twin-image elimination steps. Consequently, tomograms of scattering strength of an object can be computed by applying a filtered back-projection algorithm whose inputs are the projection images calculated by holographic reconstruction of pixel super-resolved lens-free holograms acquired at various illumination angles.

To validate the performance of the field-portable lens-free tomographic microscope, micro-beads of different dimensions as well as a Hymenolepis Nana egg, which is an infectious parasitic flatworm, were imaged. Without utilizing lenses, lasers or other costly opto-mechanical components, the presented lens-free tomographic microscope offers sectional imaging with an axial resolution of <7 μm, while also implementing pixel super-resolution that can increase the NA of each projection image up to ~0.3-0.4, over a large imaging volume of ~20 mm³. Furthermore, this volume can also be extended up to ~80 mm³ (corresponding to a DOF of ~4 mm) at the cost of reduced spatial resolution. Offering good spatial resolution over such a large imaging volume, this compact, light-weight (~110 grams) and cost-effective lens-free tomographic microscope could provide a valuable tool for telemedicine and high-throughput imaging applications in remote locations.

FIG. 15B shows a digitally synthesized pixel super-resolved (SR) hologram of a 2 μm diameter micro-particle, where holographic fringes with much higher spatial frequencies can now be observed when compared to a raw lower-resolution (LR) hologram shown in FIG. 15A. As a result of this increased numerical aperture (NA), the reconstructed images using SR holograms exhibit higher lateral resolution as revealed by the visual comparison of FIGS. 15C and 15D, where (with SR) the 2 μm bead is imaged much closer to its actual size.

Next the reconstructed depth (z) profiles were investigated corresponding to the LR and SR holograms shown in FIGS. 15A and 15B, respectively. By digitally reconstructing the LR lens-free hologram of FIG. 15A at several different depth (z) values, one can get the y-z and x-z profiles shown in FIG. 15E (images a1 and a2) corresponding to the same 2 μm particle. In these results, the broadening along the z direction illustrates the limitation of a single LR hologram toward depth sectioning. This limitation is partially improved using the SR lens-free hologram as illustrated in FIG. 15F (images b1 and b2). On the other hand, despite the numerical aperture improvement with SR, it still does not permit sectional imaging of the objects with an axial resolution of e.g., ~45 µm or better.

To mitigate this fundamental axial resolution limitation, lens-free SR holograms were used that are synthesized for ~20 illumination angles spanning a range of ±50° to create a tomogram of the same micro-particle as illustrated in FIGS. 16A-16C. These results presented in FIGS. 16A-16C indicate that the field-portable lens-free tomographic microscope significantly improves the axial resolution, which can be observed by the shortened depth-of-focus of the bead image. The field-portable tomographic microscope improves the axial resolution by a factor of >13× and ~6-7× compared to what is achievable with a single LR hologram and a single SR hologram, respectively.

To further demonstrate the depth sectioning capability of the field-portable lens-free tomographic microscope, 5 µm diameter spherical micro-beads (refractive index ~1.68, Corpuscular Inc.) were imaged that are randomly distributed within a ~50 µm thick chamber filled with an optical adhesive (refractive index ~1.52, Norland NOA65). FIGS. 17A-17E show the tomographic reconstruction results for a small region of interest that are digitally cropped from a much larger image area to match the FOV of a 40× objective lens (NA: 0.65) that is used for comparison purposes (FIGS. 17F-17J). The lens-free tomograms for the entire chamber depth were computed within <1 min using a Graphics Processing Unit (NVidia, Geforce GTX 480). Arrows in FIGS. 17A-17E indicate micro-beads that are in focus at the corresponding depth layer of the image, which can also be cross validated using conventional microscope images that are acquired at the same depths as shown in FIGS. 17F-17J. To further quantify the tomographic imaging performance, in FIG. 18A shows x and y line profiles for an arbitrary micro-bead located within the same FOV, where the full-width-at-half-maximum (FWHM) of the particle can be calculated as ~5 µm and ~5.5 µm along x and y directions, respectively, very well matching with its diameter (5 µm). The axial line-profile of the same bead tomogram (along the z direction) has a FWHM of ~12.9 µm as seen in FIG. 18B. It is important to note that, without the use of multi-angle illumination and tomographic digital reconstruction, using just a single SR hologram, the computed image of the same micro-particle would have an axial FWHM of >75 µm, which is expected for an in-line holographic imaging platform due to its long depth of focus. By taking one-dimensional spatial derivative of the axial line-profile shown in FIG. 18B (i.e., the line profile), the FWHM of the point-spread function of the tomographic microscope along the z direction can be estimated to be ~6 µm (refer to the derivative curve in FIG. 18B.

The lens-free hologram recording geometry shown in FIG. 4 has several advantages especially toward high-throughput imaging needs, achieving both a long depth-of-field (e.g., ~1-4 mm) and a wide field-of-view (e.g., ~20 mm$^2$) In specific, lens-free holographic projections can be reconstructed at any depth of interest; and the tomograms can then be computed around that depth region without introducing spatial aberrations. This approach enables 3D imaging of any arbitrary region of interest within a long depth-of-field and hence a large imaging volume.

To specifically demonstrate this capability, a multilayer chamber (four layers stacked together with ~1 mm separation in between, i.e., a total thickness of ~3.5 mm) was imaged that was composed of 10 µm beads embedded in an optical adhesive. This thick object is placed at ~0.7 mm away from the active area of the sensor-chip with its furthest layer situated at z~4.2 mm from the sensor plane. FIG. 19A illustrates the recorded hologram of the multilayer chamber at an angle of 0°. FIGS. 19B-19F illustrate the computed tomograms of different layers within this thick object, which demonstrate optical sectioning capability of the lens-free tomography approach within a long DOF. Tomograms of the entire DOF and the object volume can then be obtained by digitally merging such separate tomograms calculated at different layers. Lens-free holograms of the objects in the furthest layer (~4.2 mm away from the sensor) shift out of the sensor active area for illumination angles above 40° and below −40°, as a result of which the angular range was limited to ±40° only for the top layer. The digital implementation of the pixel super-resolution scheme for tomographic imaging of thick or multilayer chambers requires additional signal processing since objects located at significantly different depths exhibit large variations in lateral shifts of their corresponding holograms at the sensor-plane. To handle this complication, an iterative algorithm was used such that super-resolved holograms can be specifically calculated for a given depth layer (i.e., independent of the other layers). FIGS. 19G-19I illustrate SR holograms for different depths (FIG. 19G: z=~0.75 mm; FIG. 19H: z=~1.8 mm; FIG. 19I: z=~4.2 mm).

As stated above, for a chamber where the objects are distributed within a height of e.g., <200-300 µm, the holograms of all the objects shift almost equally for a given source shift. Therefore, a single SR hologram satisfying the measured data in all the sub-pixel shifted holograms can be synthesized. For thick or multilayer chambers, however, the lens-free holograms of objects that are axially separated by >200-300 µm shift considerably different amounts, and the recorded holograms for different source shifts look different. As a result, a single SR hologram to satisfy all shifted holograms cannot be calculated. To solve this issue, new holograms with the information of only the desired layers can be obtained by digitally erasing the undesired layers from the hologram intensity. To achieve this, the lens-free hologram for a thick (or multilayer) chamber as in FIG. 19A is reconstructed at the undesired layers, and the objects that are focused at those layers are removed from the hologram field using a binary masking operation. Successively deleting all the layers except the desired one yields a new digitally cleaned hologram, that is faithful to the measured data for specifically the depth layer of interest. Erasing the layers that are closer to the sensor may leave residues in the cleaned hologram, but this does not pose any problems since these residues are quite weak, and the holograms for the desired layer are still completely in agreement with the originally measured raw holographic data. Finally, once these new holograms with different sub-pixel shifts are obtained for a given layer of interest, SR hologram of that depth layer can successfully be computed. FIGS. 19G-19I illustrate digitally cleaned SR holograms at different depths.

In order to validate the performance of the field-portable lens-free tomographic microscope for potential applications in bio-medicine, a *Hymenolepis Nana* (*H. Nana*) egg was imaged. The *H. Nana* egg is an infectious parasitic flatworm of humans having an approximately spherical structure with ~40 µm diameter. Due to the long depth-of-focus of lens-free in-line holography, optical sectioning of this egg is not possible by merely reconstructing its recorded hologram at any given illumination angle. However, as demonstrated in FIG. 20A, separate depth sections (images a1, a2, a3) of this parasite egg can be created using the tomographic handheld microscope (shown in FIG. 4), exhibiting distinct details/features at each depth layer. For comparison purposes, 40× microscope images are illustrated in FIG. 20B at the same depth locations as found in FIG. 20A.

While embodiments have been shown and described, various modifications may be made without departing from the scope of the inventive concepts disclosed herein. The invention(s), therefore, should not be limited, except to the following claims, and their equivalents.

What is claimed is:

1. A hand held tomographic imager comprising:
   a hand held housing containing a sample holder configured to hold a sample with one or more objects therein;
   a plurality of partially coherent or coherent light sources disposed in the hand held housing, each of the plurality of light sources being coupled to respective waveguides that are mounted in a bridge wherein each respective waveguide is oriented at varying angles with respect to a first side of the sample;
   a microcontroller disposed in the hand held housing and operatively connected to the plurality of light sources, the microcontroller configured to selectively activate individual light sources;
   an electromagnetic actuator disposed in the hand held housing and configured to move the bridge and waveguides in substantially orthogonal directions; and
   a stationary image sensor disposed in the hand held housing on a second opposing side of the sample, wherein the waveguides are located a distance $z_1$ from the sample and wherein the image sensor is located a distance $z_2$ from the sample such that $z_2 \ll z_1$.

2. The hand held tomographic imager of claim 1, further comprising a color filter interposed between the waveguides and the sample.

3. The hand held tomographic imager of claim 1, further comprising one or more batteries disposed in the hand held housing.

4. The hand held tomographic imager of claim 1, wherein the plurality of partially coherent light sources comprise LEDs or laser diodes.

5. The hand held tomographic imager of claim 1, wherein the waveguides comprise optical fibers.

6. The hand held tomographic imager of claim 1, wherein the bridge is an arc-shaped bridge.

7. The hand held tomographic imager of claim 1, wherein the bridge has magnets mounted thereon.

* * * * *